US010703772B2

(12) United States Patent
Mundla et al.

(10) Patent No.: US 10,703,772 B2
(45) Date of Patent: Jul. 7, 2020

(54) PROCESSES FOR THE PREPARATION OF SGLT-2 INHIBITORS, INTERMEDIATES THEREOF

(71) Applicant: Emmennar Pharma Private Limited, Hyderabad (IN)

(72) Inventors: Maha Vishnu Mundla, Hyderabad (IN); Sridhar Malyala, Hyderabad (IN); Chandra Prakash Narani, Rangareddy (IN); Laxmi Narasimha Varaprasad Chintaginjala, Hyderabad (IN); Suresh Kumar Gunukula, Secunderabad (IN); Bala Yellaiah Chittiboyina, Hyderabad (IN); Prabhakar Bellam, Hyderabad (IN); Hemalatha Reddy Samireddy, Secunderabad (IN); Sowmya Dantham, Hyderabad (IN); Prasad Vure, Hyderabad (IN); Pooja Kale, Rangareddy (IN)

(73) Assignee: Emmennar Pharma Private Limited, Telangana (IN)

( * ) Notice: Subject to any disclaimer, the term of this patent is extended or adjusted under 35 U.S.C. 154(b) by 0 days.

(21) Appl. No.: 15/990,860

(22) Filed: May 29, 2018

(65) Prior Publication Data

US 2018/0346502 A1 Dec. 6, 2018

(30) Foreign Application Priority Data

| May 30, 2017 | (IN) | ............................. 201741018925 |
| Dec. 1, 2017 | (IN) | ............................. 201741043165 |
| May 9, 2018 | (IN) | ............................. 201841017424 |

(51) Int. Cl.

| *A01N 43/04* | (2006.01) |
| *A61K 31/70* | (2006.01) |
| *C07H 7/04* | (2006.01) |
| *C07C 41/18* | (2006.01) |
| *C07H 7/06* | (2006.01) |
| *A61K 47/38* | (2006.01) |
| *C07D 307/20* | (2006.01) |
| *A61K 9/10* | (2006.01) |
| *A61K 9/14* | (2006.01) |

(52) U.S. Cl.
CPC ................. *C07H 7/04* (2013.01); *A61K 9/10* (2013.01); *A61K 9/146* (2013.01); *A61K 47/38* (2013.01); *C07C 41/18* (2013.01); *C07D 307/20* (2013.01); *C07H 7/06* (2013.01); *C07B 2200/07* (2013.01)

(58) Field of Classification Search
None
See application file for complete search history.

(56) References Cited

U.S. PATENT DOCUMENTS

| 9,902,751 | B2 * | 2/2018 | Kaushik .................. C07H 1/00 |
| 2017/0247356 | A1 | 8/2017 | Desai et al. |
| 2017/0319539 | A1 * | 11/2017 | Jetti .................... C07D 407/12 |
| 2018/0127391 | A1 | 5/2018 | Bhirud et al. |

FOREIGN PATENT DOCUMENTS

| IN | 6139/CHE/2013 A1 | 6/2016 |
| IN | 1790/MUM/2015 A1 | 4/2017 |
| IN | 4286/MUM/2015 A1 | 11/2017 |
| IN | 201621021804 A1 | 12/2017 |
| IN | 201641022864 A1 | 1/2018 |
| IN | 201741001520 A1 | 7/2018 |

OTHER PUBLICATIONS

Xu et al. J. Med. Chem. (2014), vol. 57, pp. 1236-1251.*

* cited by examiner

*Primary Examiner* — Patrick T Lewis
(74) *Attorney, Agent, or Firm* — Carrier Blackman & Associates, P.C.; Joseph P. Carrier; Fulchand P. Shende

(57) ABSTRACT

The present invention relates to novel, improved processes for the preparation of sodium glucose co-transporter 2 (SGLT-2) inhibitors and novel intermediates thereof. More particularly, the present invention relates to a novel, improved process for the preparation of gliflozin compounds such as empagliflozin and dapagliflozin, intermediates thereof. The product obtained from the processes of present invention may be amorphous or crystalline, or in the form of amorphous/crystalline solid dispersions/solutions with pharmaceutically acceptable polymers and preparation process thereof. Also, the products obtained from the present invention may be used for the preparation of medicaments for the prevention and/or treatment of diseases and conditions associated with SGLT-2 inhibition.

12 Claims, 3 Drawing Sheets

PROCESSES FOR THE PREPARATION OF SGLT-2 INHIBITORS, INTERMEDIATES THEREOF

CROSS-REFERENCE TO RELATED APPLICATIONS

The present application claims the benefit of priority of our Indian provisional patent application No. 201741018925 filed on May 30, 2017; Indian provisional patent application No. 201741043165 filed on Dec. 1, 2017; and Indian provisional patent application No. 201841017424 filed on May 9, 2018 which are incorporated herein by reference.

FIELD OF INVENTION

The present invention relates to novel, improved processes for the preparation of sodium glucose co-transporter 2 (SGLT-2) inhibitors and novel intermediates thereof. More particularly, the present invention relates to a novel, improved process for the preparation of gliflozin compounds such as empagliflozin and dapagliflozin, intermediates thereof. Also, the products obtained from the present invention may be used for the preparation of medicaments for the prevention and/or treatment of diseases and conditions in which SGLT-2 inhibitors are indicated.

BACKGROUND OF THE INVENTION

Empagliflozin is a SGLT-2 inhibitor with a chemical name (1S)-1,5-anhydro-1-C-[4-chloro-3-[[4-[[(3S)-tetrahydro-3-furanyl]oxy]phenyl]methyl]phenyl]-D-glucitol and has the following structural formula:

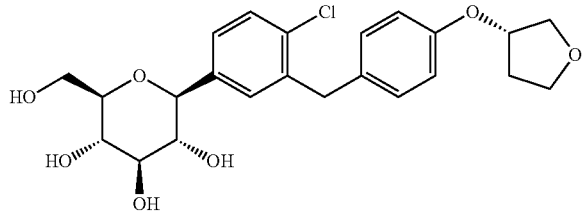 [SMILES: OC[C@H]1O[C@@H](c2ccc(Cl)c(Cc3ccc(O[C@H]4CCOC4)cc3)c2)[C@H](O)[C@@H](O)[C@@H]1O]

It was approved by the FDA in August, 2014 in the form of oral tablets for human use under the proprietary name, JARDIANCE® indicated as an adjunct to diet and exercise to improve glycemic control in adults with type 2 diabetes mellitus; and to reduce the risk of cardiovascular death in adult patients with type 2 diabetes mellitus and established cardiovascular disease.

Dapagliflozin is an orally active SGLT-2 inhibitor, approved by the FDA in January, 2014 in the form of oral tablets for human use under the proprietary name, FARXIGA®. The active ingredient of the approved product is chemically designated as (1S)-1,5-anhydro-1-C-[4-chloro-3-[(4-ethoxyphenyl)methyl] phenyl]-D-glucitol, (2S)-propylene glycol monohydrate and is marketed for the treatment of type 2 diabetes mellitus. The empirical formula is $C_{21}H_{25}ClO_6 \cdot C_3H_8O_2 \cdot H_2O$ and the molecular weight is 502.98. The structural formula is:

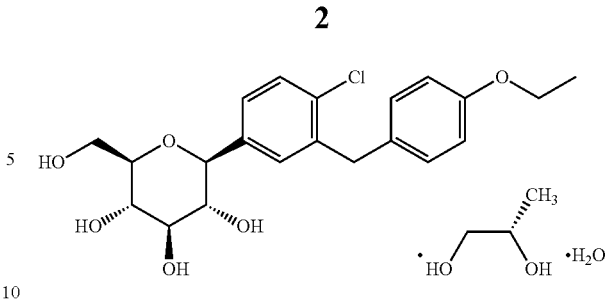

Several methods are known in the art for the synthesis of SGLT-2 inhibitors.

PCT publication No. WO 2005/092877 discloses glucopyranosyl-substituted benzene derivative, (1S)-1,5-anhydro-1-C-[4-chloro-3-[[4-[[(3S)-tetrahydro-3-furanyl]oxy]phenyl]methyl]phenyl]-D-glucitol (empagliflozin), and preparation process thereof, wherein 4-bromo-1-chloro-2-(4-methoxybenzyl)-benzene is reacted with boron tribromide ($BBr_3$) in dichloromethane to produce 4-(5-bromo-2-chloro-benzyl)-phenol which is reacted with t-butyl dimethyl silyl chloride in dichloromethane in the presence of triethylamine and N,N-dimethylaminopyridine to get [4-(5-bromo-2-chloro-benzyl)-phenoxy]-tert-butyldimethylsilane which is further reacted with n-butyllithium in tetrahydrofuran (THF) followed by condensation with 2,3,4,6-tetrakis-O-(trimethylsilyl)-D-glucopyranone. The resulting solution is reacted with methane sulfonic acid in methanol followed by reduction with triethylsilane and boron trifluoride etherate and acylated with acetic anhydride/pyridine in dichloromethane followed by treating with potassium hydroxide in methanol to produce phenolic intermediate. This phenolic intermediate is reacted with (R)-tetrahydrofuran-3-yl-4-methylbenzenesulfonate to produce empagliflozin.

The above process involves the use of hazardous boron tribromide as it reacts violently and decomposes to toxic compounds when on contact with moisture.

International patent application, WO/2017/130217 describes a process for preparing empagliflozin, wherein the process for preparing 4-bromo-1-chloro-2-(4-methoxybenzyl)benzene comprises reducing (5-bromo-2-chlorophenyl)(4-methoxy phenyl)methanone using titanium tetrachloride and triethylsilane. Further, (2R,3R,4R,5S,6S)-2-(acetoxymethyl)-6-(4-chloro-3-(4-hydroxybenzyl)phenyl)tetrahydro-2H-pyran-3,4,5-triyl triacetate is treated with (R)-tetrahydrofuran-3-yl 4-nitrobenzenesulfonate in DMF, followed by deprotection to yield empagliflozin.

Titanium tetrachloride ($TiCl_4$) is a strong Lewis acid, exothermically forming adducts with even weak bases such as THF and explosively with water and releasing HCl. (R)-tetrahydrofuran-3-yl-4-nitrobenzenesulfonate is not commercially available and its synthesis requires use of expensive starting materials, thereby increasing the raw material cost. This process may not be useful for economic production of empagliflozin.

International patent application, WO/2017/203457 discloses a process for preparing empagliflozin comprising reacting (R)-tetrahydrofuran-3-yl-4-methyl benzenesulfonate with (2S,3R,4R,5S,6R)-2-(4-chloro-3-(4-hydroxybenzyl)phenyl)-6-(hydroxymethyl)tetrahydro-2H-pyran-3,4,5-triol to yield empagliflozin.

However, the process for preparing compound (4-(2-chloro-5-iodobenzyl) phenoxy)(tert-butyl)dimethylsilane, involves multiple steps and makes use of expensive reagents such as 1,1,3,3-tetramethyldisiloxane (TMDS), tert-butyldimethylsilyl chloride (TBDMSCl) and use of cesium carbonate in preparing empagliflozin, thereby making it uneconomical.

U.S. Pat. Nos. 6,515,117; 7,375,213; 7,932,379; and 7,919,598 disclose processes for the preparation of dapagliflozin comprising the step of hydrolyzing an acetylated dapagliflozin, in the presence of an alkali metal hydroxide such as lithium hydroxide or sodium hydroxide to give pure dapagliflozin as an amorphous glassy off-white solid with a purity of 94%.

U.S. Pat. No. 8,952,139 discloses an alternate process for preparation of dapagliflozin by coupling 1,6-anhydro-2,4-di-O-tert-butyldiphenylsilyl-8-D-gluco pyranose with 4-chloro-3-[(4-ethoxyphenyl)methyl]phenyl magnesium bromide to yield (2S,3R,4R,5S,6R)-2-(4-chloro-3-(4-ethoxybenzyl)phenyl)-3,5-bis(2,2-dimethyl-1,1-diphenyl-propoxy)-6-(hydroxymethyl)tetrahydro-2H-pyran-4-ol followed by removal of protecting groups in tetrahydrofuran (THF) in the presence of TBAF and calcium carbonate to yield dapagliflozin.

Inefficiencies known in the art for preparing SGLT-2 inhibitors include (1) a lack of stereo selectivity during formation of the desired β-anomer of the C-arylglucoside, (2) relatively long synthetic routes (linear syntheses), (3) uneconomic protection of hydroxyl groups, (4) use of hazardous reagents, and/or (5) complex work-up procedures and (6) use of expensive raw materials.

Hence, there exists a continuous need for alternate, improved, safe and cost effective synthetic routes for the preparation of SGLT-2 inhibitors, with high chemical and enantiomeric purity, applicable for large scale production.

The present invention provides novel, improved processes which are convergent syntheses for the preparation of SGLT-2 inhibitors particularly empagliflozin and dapagliflozin, which are cost effective, non-hazardous, less cumbersome, advantageous over prior art, involving simplified work-up procedures with high yields, better enantiomeric purity and are commercially scalable in industry.

SUMMARY OF INVENTION

The present invention provides novel, improved processes and intermediates for the preparation of SGLT-2 inhibitors, preferably gliflozins, namely empagliflozin and dapagliflozin.

In one embodiment, the present invention provides a novel process for the preparation of (1S)-1,5-anhydro-1-C-[4-chloro-3-[[4-[[(3S)-tetrahydro-3-furanyl]oxy]phenyl]methyl]phenyl]-D-glucitol, i.e., empagliflozin, said process comprising coupling a compound of formula VI, with tetrahydrofuran-3-ol of desired configuration in the presence of a base and suitable solvent, followed by in situ hydrolysis of the resulting compound of formula VIIa to isolate a compound of formula VII, which is further reacted with a reducing agent to give empagliflozin represented as follows:

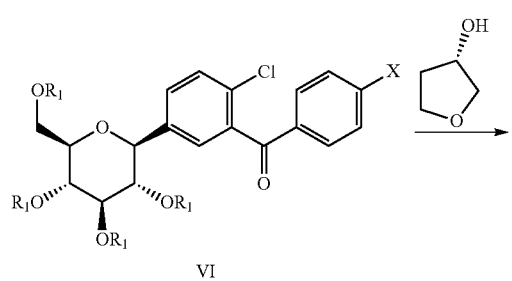

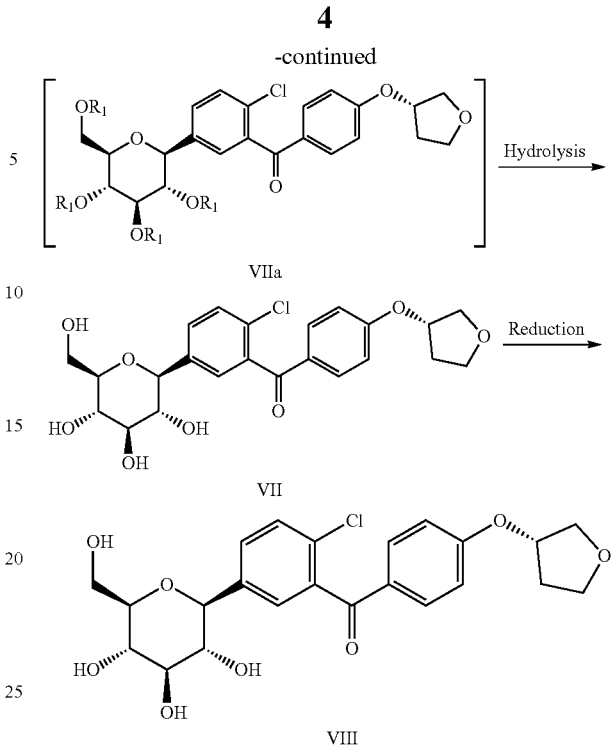

Wherein in a compound of formula VI, X is a leaving group (selected from halogen, mesylate, tosylate, brosylate, besylate, nosylate and triflate) and $R_1$ is a hydroxyl protecting group.

Alternatively, the novel process of the present invention for preparing empagliflozin comprises exhaustive reduction of isolated compound of formula VIIa to obtain empagliflozin,

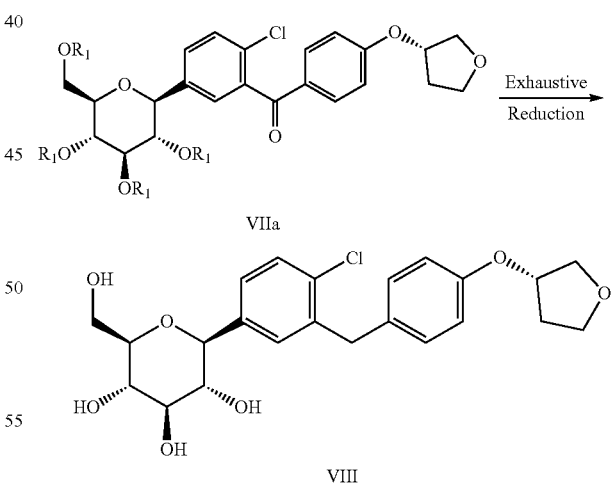

In a second embodiment, the present invention provides a novel process for the preparation of (1S)-1,5-anhydro-1-C-[4-chloro-3-[[4-[[(3S)-tetrahydro-3-furanyl]oxy]phenyl]methyl]phenyl]-D-glucitol i.e., empagliflozin, wherein the process comprises reacting compound (7) in an alcoholic solvent with compound (8) in the presence of a base, represented as follows:

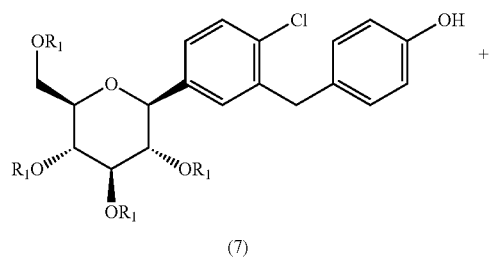

(7)

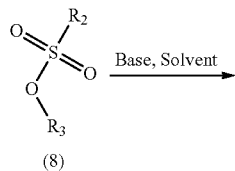

(8)

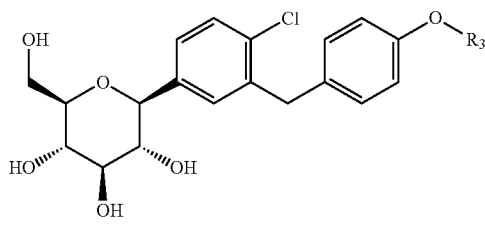

(9)

Wherein $R_1$ is hydrogen or a hydroxyl protecting group, preferably an acyl group, $R_2$ is selected from trifluoromethyl, $C_{1-6}$ alkyl, or an aryl group optionally substituted at para position with groups such as halogen, $C_{1-6}$ alkyl and $R_3$ is tetrahydrofuran-3-yl. In one preferred embodiment, $R_2$ is $C_{1-6}$ alkyl, preferably methyl. In another preferred embodiment, $R_2$ is a phenyl group. In another embodiment, $R_2$ is phenyl substituted with a $C_{1-6}$ alkyl, preferably methyl on para position.

In a third embodiment, the novel process of the present invention provides preparing a compound of formula (8), comprising reacting a compound v with compound ii in the presence of a base and solvent to obtain compound (8) in desired configuration, wherein $R_2$ is defined as hereinbefore.

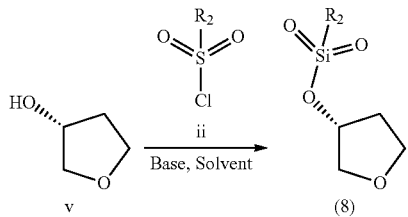

In a fourth embodiment, the present invention provides an improved process for preparing (1S)-1,5-anhydro-1-C-[4-chloro-3-[(4-ethoxyphenyl)methyl]phenyl]-D-glucitol i.e., dapagliflozin, comprising reacting a compound (7) in a suitable solvent with compound (8) in the presence of a base, represented as follows:

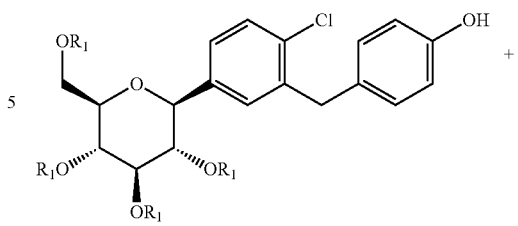

(7)

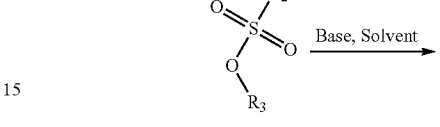

(8)

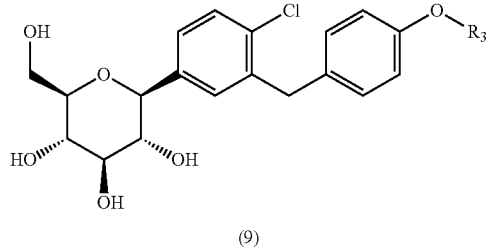

(9)

Wherein $R_1$ is hydrogen or a hydroxyl protecting group, $R_2$ is trifluoromethyl, $C_{1-6}$ alkyl, or an aryl group optionally substituted at para position with groups such as halogen, $C_{1-6}$ alkyl and $R_3$ is ethyl.

In a fourth embodiment, the novel processes of the present invention provide amorphous empagliflozin characterized by a purity of about 99% or more by HPLC, free of any residual solvents and stable for 12 months on storage at 5±3° C.

In a fifth embodiment, the novel processes of the present invention provide empagliflozin in the form of amorphous solid dispersions/solutions with pharmaceutically acceptable polymers, characterized by a purity of about 99% or more by HPLC, free of any residual solvents, stable for 6 months on storage conditions at 25±2° C. with a relative humidity (RH) of 60%±5%. In preferred embodiments, amorphous solid dispersions of empagliflozin with ethyl cellulose and hydroxypropyl cellulose are provided.

DETAILED DESCRIPTION OF THE INVENTION

Figure 1:
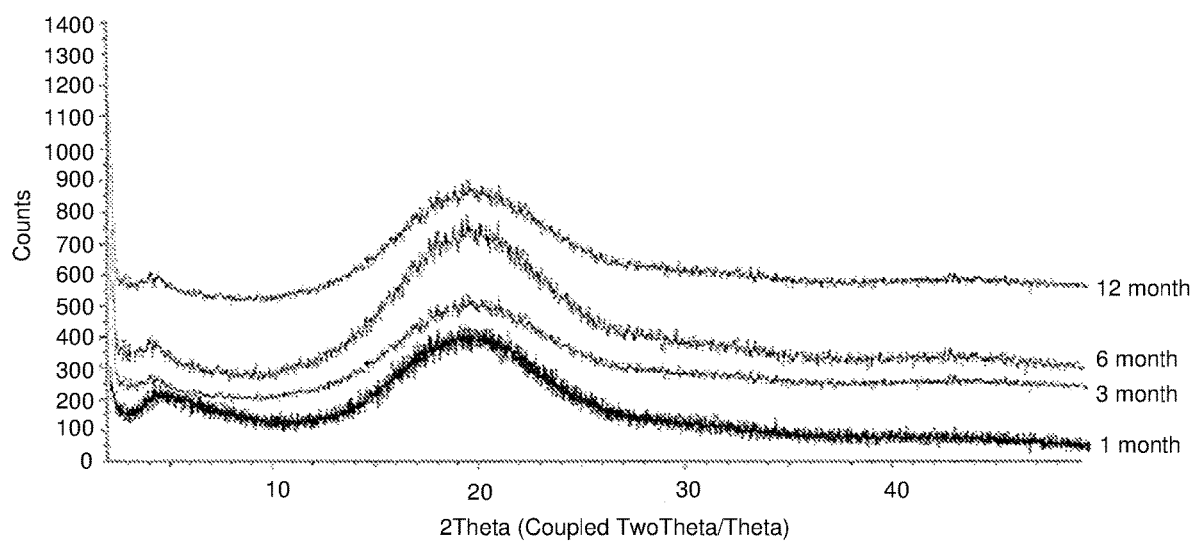
FIG. 1 represents an overlay of powder X-ray diffraction pattern of an amorphous empagliflozin at $1^{st}$, $3^{rd}$, $6^{th}$ and $12^{th}$ months.

The present inventors have surprisingly found novel, improved cost-effective processes for preparing SGLT-2 inhibitors, particularly empagliflozin, dapagliflozin and novel intermediates thereof, which are commercially scalable with high enantiomeric purity and better yields with low technical expenditure.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, the term "SGLT-2" refers to sodium glucose co-transporter 2, which is a sodium dependent glucose transport protein. SGLT-2 is the primary co-transporter involved in renal glucose reabsorption. As used herein, "SGLT-2 inhibitor" refers to any molecule that can modulate SGLT-2 activity in vitro or in vivo.

The term "medicament" as used herein refers to a pharmaceutical composition containing the SGLT-2 inhibitor compounds prepared by the present invention, wherein the pharmaceutical composition may be used for human or non-human therapy of various diseases or disorders in a therapeutically effective dose.

The term "treatment" as used herein is defined as the management and care of a patient, e.g. a mammal, a human, for combating the disease, condition or disorder and includes the administration of SGLT-2 inhibitors to prevent the onset of the symptoms or complications or alleviating the symptoms or complications or eliminating the disease, condition or disorder.

As used herein, the term "protecting group" refers to a compound that is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry [See e.g. Greene's Protective Groups in Organic Synthesis by T. W. Greene and P. G. M. Wuts, 4th Edition; John Wiley & Sons, New York (2007)].

As used herein, the term "leaving group" refers to an atom or group of atoms which breaks away from the rest of the molecule, taking with it the electron pair which used to be the bond between the leaving group and the rest of the molecule. According to the present invention, the leaving groups include without limitation, halides such as fluoride, chloride, bromide and iodide, and sulfonate esters such as mesylate (OMs), tosylate (OTs), brosylate (OBs), besylate (OBS), nosylate (ONs) and triflate (OTf).

The term "exhaustive reduction" as used herein refers to the reduction of all carbonyl C—O bonds including keto and ester groups in the molecule.

The terms such as "about", "substantially," and the like are to be construed as modifying a term or value such that it is not an absolute. Such terms will be defined by the circumstances and the terms that they modify as those terms are understood by those skilled in the art. This includes, at very least, the degree of expected experimental error, technique error and instrument error for a given technique used to measure a value.

As used herein, the term "solid dispersion" or "solid solution" means any solid composition having at least two components, wherein one component is dispersed homogeneously throughout the other component or components. For the purpose of the present invention, the terms "solid dispersion" and "solid solution" are herein used interchangeably. In certain embodiments, a solid dispersion as disclosed herein includes empagliflozin dispersed among at least one other component, such as a pharmaceutically acceptable polymer.

The term "amorphous solid dispersion" as used herein, refers to stable solid dispersions comprising drug substance and a polymer matrix, wherein the drug substance may be amorphous or crystalline.

The term "pharmaceutically acceptable" as used herein means suited for normal pharmaceutical applications, i.e., giving rise to no adverse events in patients etc.

The term "free from residual solvents" as used herein means residual solvents are within the permissible ICH (International Council for Harmonization) limits suitable for pharmaceutical preparations.

The term "substantially pure" or "substantially pure amorphous" as used herein refers to polymorphic purity of amorphous empagliflozin or amorphous solid dispersion having a purity of about 95% or more, more preferably 97% or more, most preferably 99.5% or more. The amorphous forms may comprise less than 5%, 3%, 1% of any other crystalline form. More preferably, the amorphous forms may comprise less than 0.5% of any other crystalline form. Most preferably, the amorphous form/amorphous solid dispersion of empagliflozin may not show any detectable amount of any crystalline form.

In a first embodiment, the present invention relates to a new process for the preparation of empagliflozin, (1S)-1,5-anhydro-1-C-[4-chloro-3-[[4-[[(3S)-tetrahydro-3-furanyl]oxy]phenyl] methyl]phenyl]-D-glucitol, wherein the process comprises the following steps:

(a) Treating a compound of formula V with a compound B to obtain a compound of formula VI;

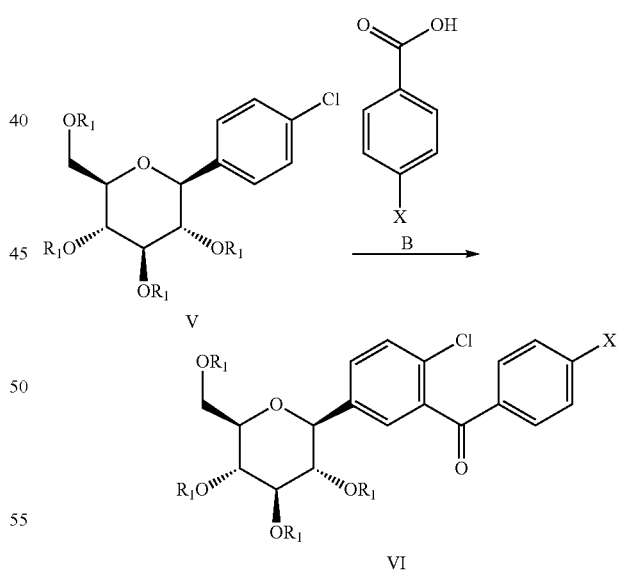

Wherein in a compound of formula V, $R_1$ is a hydroxyl protecting group selected from acyl (acetyl, propionyl, pivaloyl, benzoyl) groups, and in a compound B, X is a leaving group selected from halogen (fluorine, chlorine, bromine, iodine), mesylate, tosylate, brosylate, besylate, nosylate and triflate;

(b) 1. Coupling the compound of formula VI with tetrahydrofuran-3-ol (C) to obtain a compound of formula VIa, without being isolated;

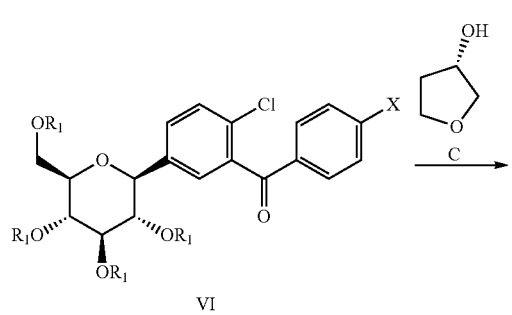

VI

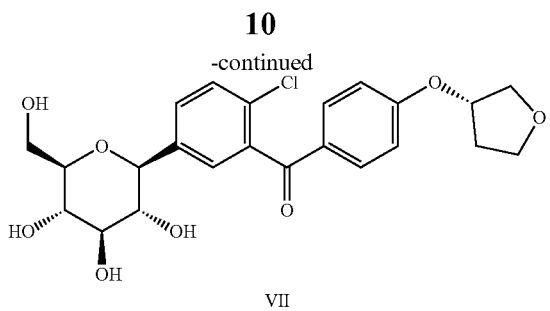

VII (d) 1. Reducing the compound of formula VII with a reducing agent to yield empagliflozin

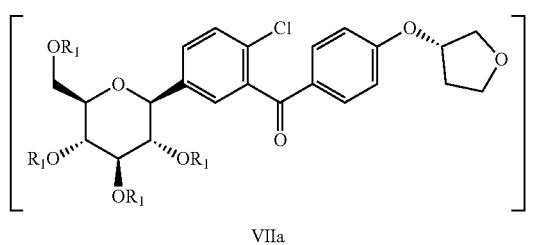

VIIa (or)
(b) 2. Coupling the compound of formula VI with tetrahydrofuran-3-ol (C) to isolate a compound of formula VIIa;

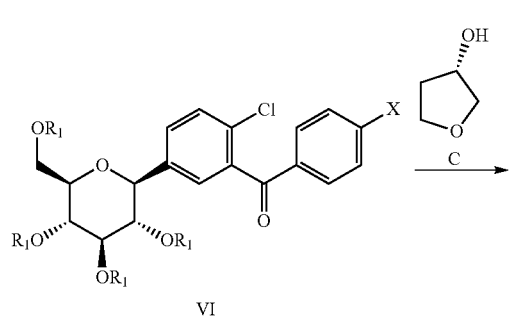

VI

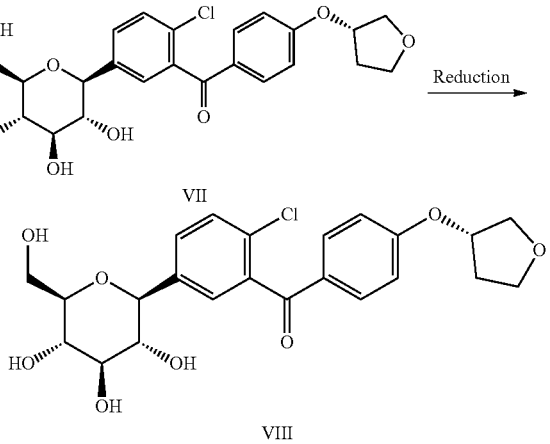

VII

VIII (or)
(d) 2. Subjecting the compound obtained from step (b) 2 to exhaustive reduction to obtain empagliflozin.

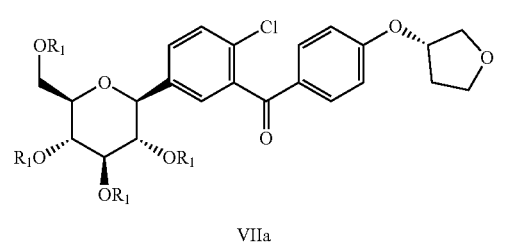

VIIa (c) In-situ hydrolyzing the compound of formula VIIa from step (b) 1 to obtain a compound of formula VII;

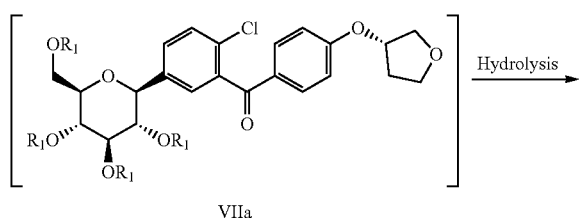

VIIa

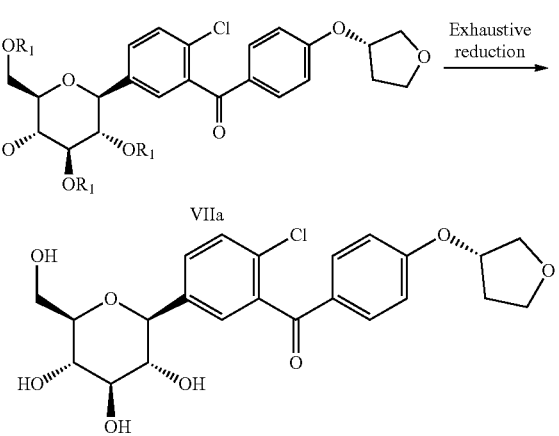

VIIa

VIII

Wherein in the above reaction steps, $R_1$ and X are defined as hereinbefore.

In step (a), the compound B is converted to corresponding acyl halide using reagents selected from thionyl chloride, sulfuryl chloride, phosphorus trichloride, phosphorus oxychloride, phosphorus pentachloride, oxalyl chloride, acetyl chloride.

The reaction is carried out in the presence of a Lewis acid and solvents described as hereinafter; and at temperature ranging from about 0° C. to solvent reflux temperature. The solvent may be selected in the view of the Lewis acid used.

In steps (b) 1 and (b) 2, the reaction is carried out using a solvent in the presence of a suitable base at a temperature of about 80° C. to 100° C. The compound of formula VIIa may or may not be isolated.

In step (c), the hydroxyl protecting groups may be cleaved for example hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide, potassium hydroxide or alkali metal carbonates such as lithium carbonate, sodium carbonate, potassium carbonate, cesium carbonate or amine derivatives such as, ammonia, methylamine, dimethylamine or aprotically, e.g. in the presence of iodotrimethylsilane, at temperatures between 0 and 120° C., preferably at temperatures between 10 and 100° C.

In steps (d) 1 and (d) 2, the reduction may be conducted with a reducing agent in the presence of or without a Lewis acid. Preferred reaction temperatures are between −80° C. and 120° C., more preferably between −30 and 80° C.

The compound of formula V may be prepared according to the methods reported in the literature, see *J. Org. Chem.*, 2007, 72 (25), pp 9746-9749.

In preferred embodiments, the novel process of the present invention may be presented in Scheme A.

In the present disclosure, the novel process of the present invention for preparing empagliflozin provides the following novel compounds useful as intermediates:

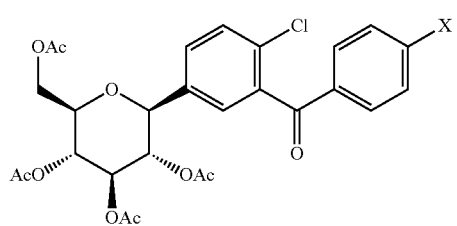
VIa

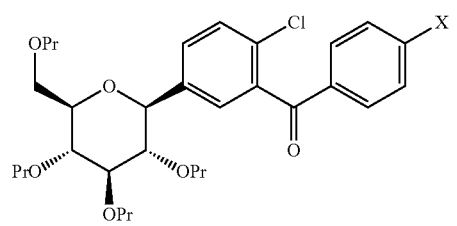
VIb

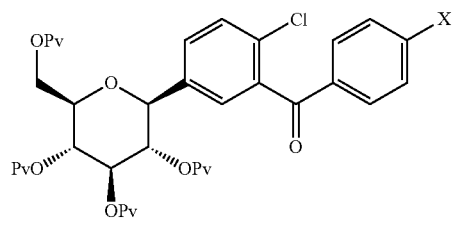
VIc

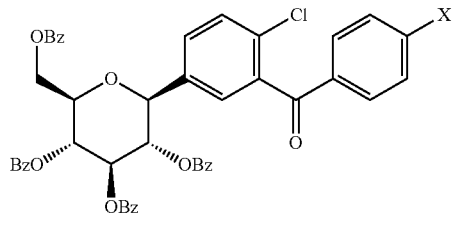
VId

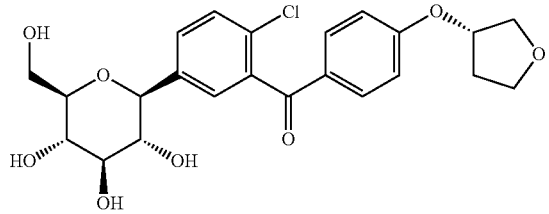
VII

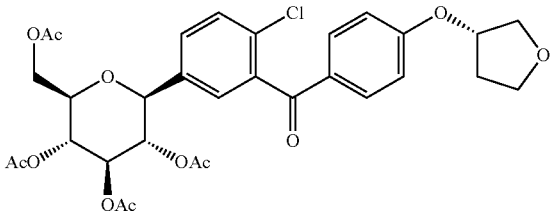
VIIa

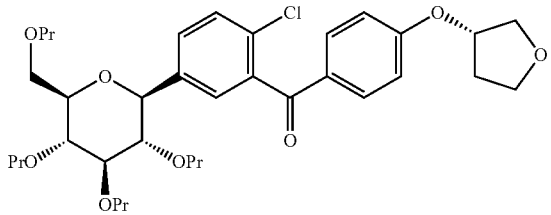
VIIb

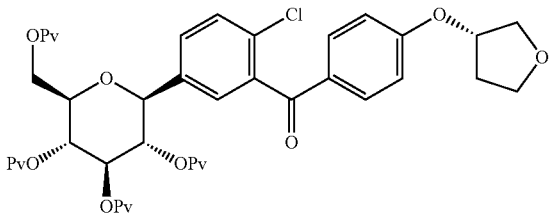
VIIc

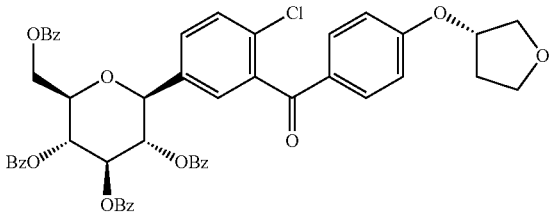
VIId where X=F, Cl, I, OMs, OTs, OBs, OBS, ONs, OTf

Ac=Acetyl, Pr=Propionyl, Pv=Pivaloyl, Bz=Benzoyl

Scheme A

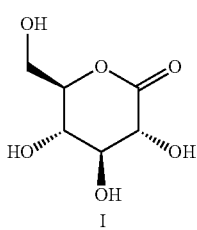
I

Trimethylsilyl chloride
N-methylmorpoline
Tetrahydrofuran

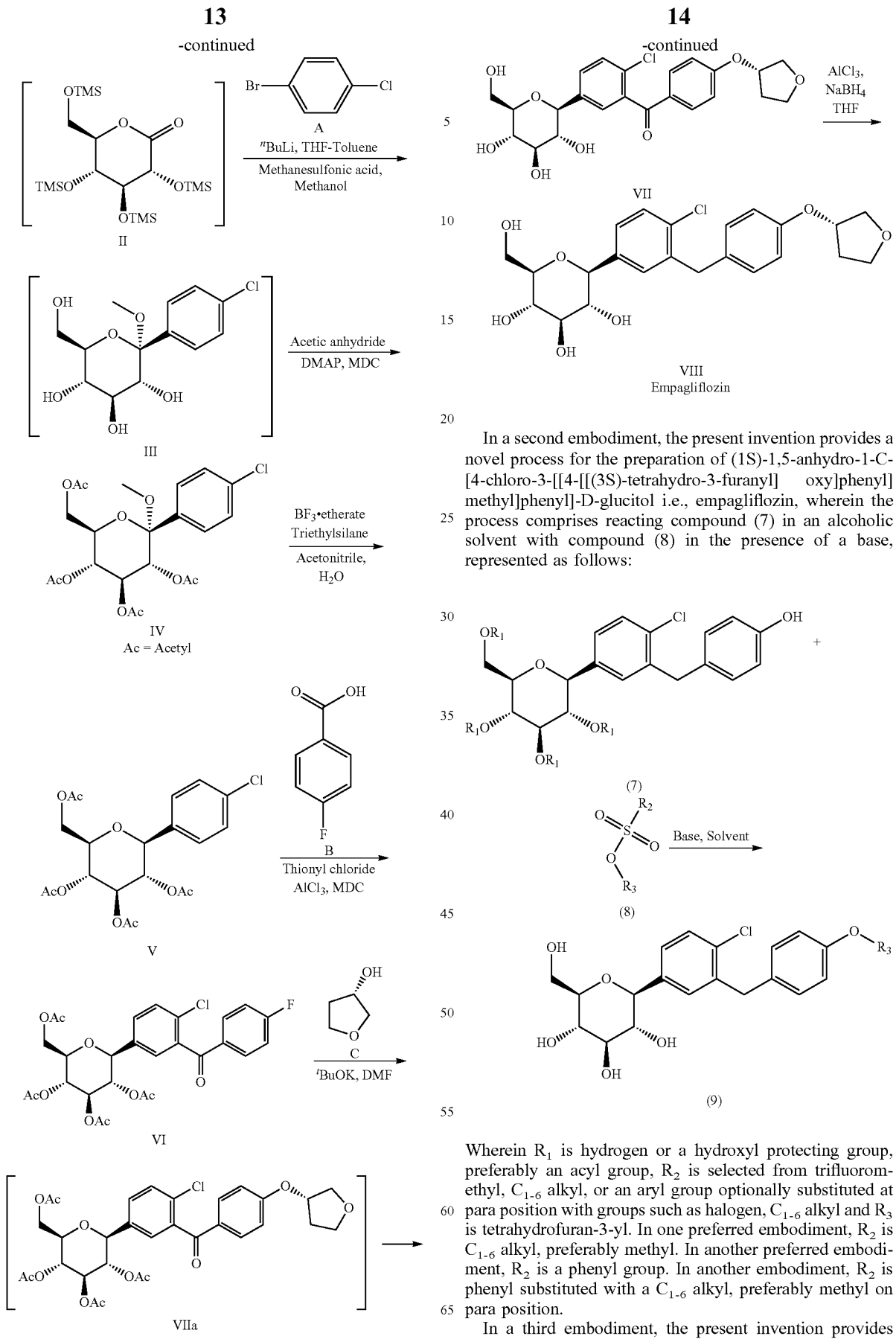

In a second embodiment, the present invention provides a novel process for the preparation of (1S)-1,5-anhydro-1-C-[4-chloro-3-[[4-[[(3S)-tetrahydro-3-furanyl] oxy]phenyl] methyl]phenyl]-D-glucitol i.e., empagliflozin, wherein the process comprises reacting compound (7) in an alcoholic solvent with compound (8) in the presence of a base, represented as follows:

Wherein $R_1$ is hydrogen or a hydroxyl protecting group, preferably an acyl group, $R_2$ is selected from trifluoromethyl, $C_{1-6}$ alkyl, or an aryl group optionally substituted at para position with groups such as halogen, $C_{1-6}$ alkyl and $R_3$ is tetrahydrofuran-3-yl. In one preferred embodiment, $R_2$ is $C_{1-6}$ alkyl, preferably methyl. In another preferred embodiment, $R_2$ is a phenyl group. In another embodiment, $R_2$ is phenyl substituted with a $C_{1-6}$ alkyl, preferably methyl on para position.

In a third embodiment, the present invention provides improved, industrially viable process for preparing (1S)-1, 5-anhydro-1-C-[4-chloro-3-[(4-ethoxyphenyl) methyl]phenyl]-D-glucitol i.e., dapagliflozin or solvates or hydrates thereof, wherein the process comprises reacting compound (7) in a suitable solvent with compound (8) in the presence of a base to form compound (9);

In an alternative embodiment, where $R_1$ is a hydroxyl protecting group, compound (7) in a suitable solvent is reacted with compound (8) in the presence of a base, where $R_2$ and $R_3$ are defined as hereinbefore to form an adduct, which is further subjected to deprotection to yield empagliflozin or dapagliflozin respectively.

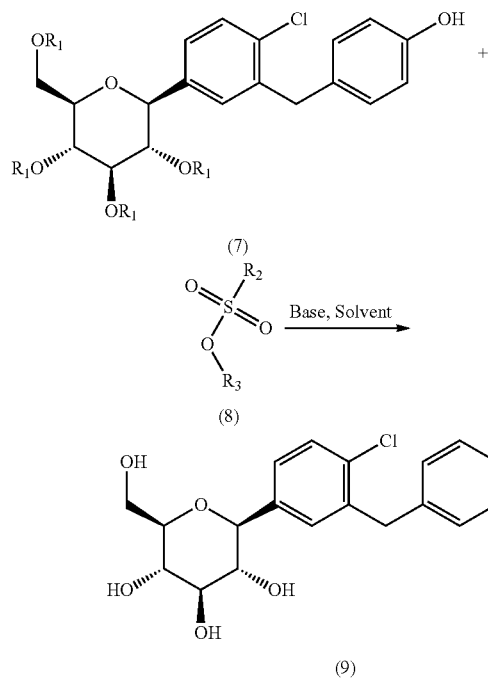

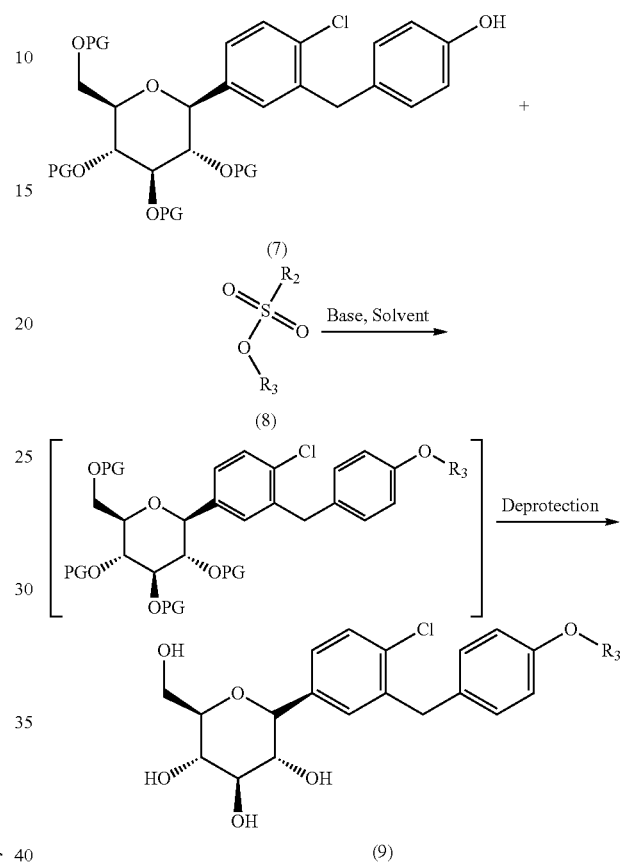

Wherein $R_1$ is hydrogen or a hydroxyl protecting group, $R_2$ is selected from trifluoromethyl, $C_{1-6}$ alkyl, or an aryl group optionally substituted at para position with groups such as halogen, $C_{1-6}$ alkyl and $R_3$ is ethyl.

According to the present disclosure, the hydroxyl protecting group (PG) is selected from the group consisting of acetyl (Ac), propionyl, benzyl (Bn), 2-nitrobenzyl, 4-nitrobenzyl, p-methoxybenzyl (PMB), p-methoxybenzylcarbonyl (Moz or MeOZ), 2,3-dimethoxybenzyl, 2,4-dimethoxybenzyl, 3,4-dimethoxybenzyl, benzoyl (Bz), benzyloxycarbonyl(Cbz), p-methoxybenzyloxycarbonyl, carboethoxy, carbomethoxy, t-butoxycarbonyl (BOC), 2,2,2-trichloroethoxycarbonyl (Troc), 2-(trimethylsilyl) ethoxycarbonyl (Teoc), 2-(4-trifluoromethylphenylsulfonyl)ethoxy carbonyl (Tsc), tri(C1-4-alkyl)silyl, tert-butyldimethylsilyl (TBDMS), tertbutyldiphenylsilyl (TBDPS), methoxymethyl ether, 2-tetrahydropyranyl (THP), allylether, 9-fluorenylmethyl, 9-fluorenylmethyloxycarbonyl (FMOC), 1-adamantyloxycarbonyl (Adoc), 2-adamantyl carbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-phenylsulfonyl ethyl, diphenyl-4-pyridylmethyl, N',N'-dimethylhydrazinyl, t-butoxymethyl (Bum), benzyloxymethyl (BOM), 1-(ethoxy)ethyl, triphenylmethyl, diphenylmethyl, N-pivaloyloxymethyl (POM), 1,1-diethoxymethyl. In preferred embodiments of the invention, $R_1$ is hydrogen or acetyl (Ac) and $R_2$ is an aryl group preferably phenyl.

In one embodiment, where $R_1$ is hydrogen, compound (7) in a suitable solvent is reacted with compound (8) in the presence of a base, where $R_2$ and $R_3$ are defined as hereinbefore to form empagliflozin or dapagliflozin respectively.

Deprotection may be carried out in the presence of a base or an acid. Preferably the base is same as used hereinbefore. The acid may be selected from mineral and organic acids such as hydrochloric acid, hydrobromic acid, sulphuric acid, acetic acid, formic acid or mixtures thereof.

The reaction of compound (7) with compound (8) may be carried out at temperature of about 75-90° C.

In a fourth embodiment, present invention provides a cost-effective process for preparing the compound (7), useful as a common intermediate for preparing empagliflozin as well as dapagliflozin and said process comprises:

(a) reacting a diphenylketone compound (1) with a reducing agent in the presence of a Lewis acid and a solvent to obtain diphenylmethane compound (2);

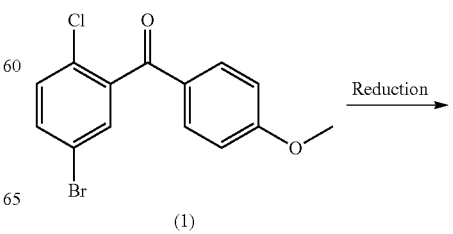

-continued

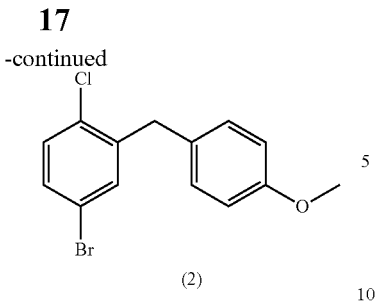

(2)

(b) coupling diphenylmethane compound (2) with the protected gluconolactone (3) in the presence of an alkyl lithium and suitable solvent followed by treatment with an acid to obtain compound (4), wherein in compound (3), PG is a hydroxyl protecting group, preferably trimethylsilyl;

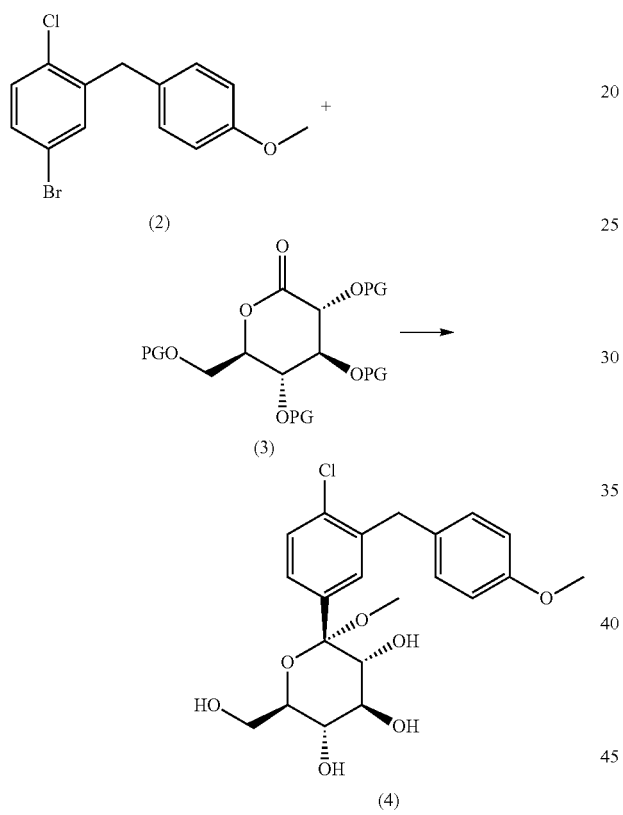

(c.1) treating compound (4) with a suitable reagent in the presence of a base, wherein the hydroxy groups are protected to form compound (5), wherein PG denotes a hydroxyl protecting group, preferably acetyl;

-continued

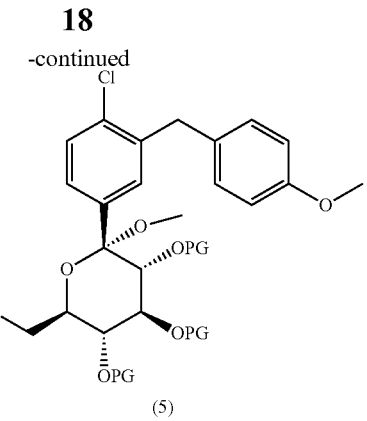

(5)

(or)

(c.2) compound (4) obtained from step (b) is subjected to reduction to obtain compound 5a;

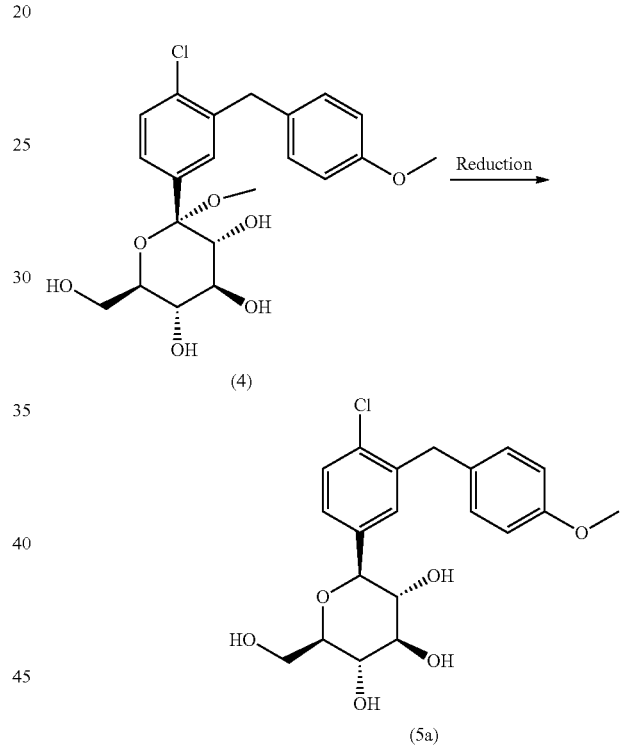

(d.1) compound (5) from step (c.1) is further reacted with a reducing agent in the presence of a Lewis acid and a suitable solvent to form compound (6);

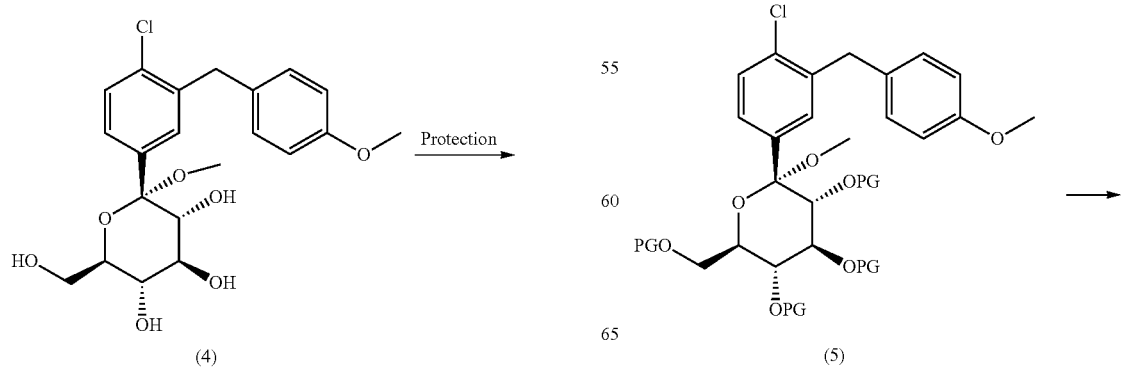

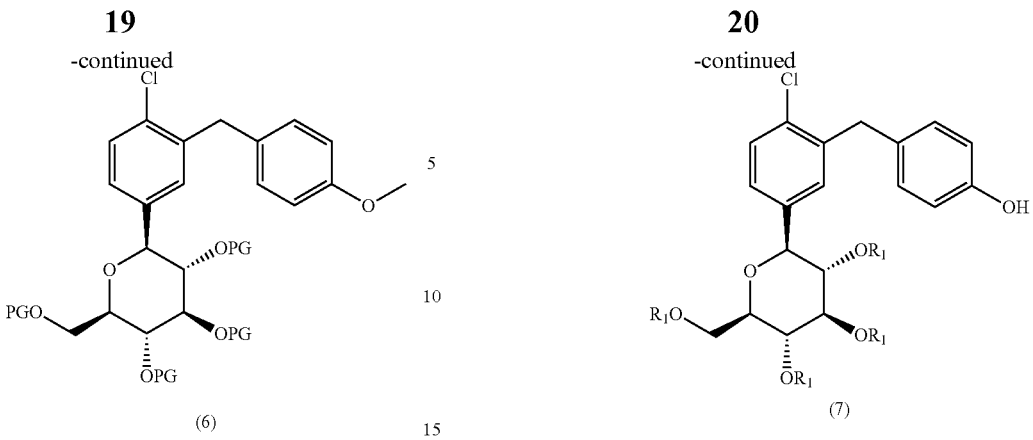

(or)

(d.2) compound (5a) obtained from step (c.2) is reacted with suitable reagent to protect the hydroxy groups in the presence of a base to form compound (6);

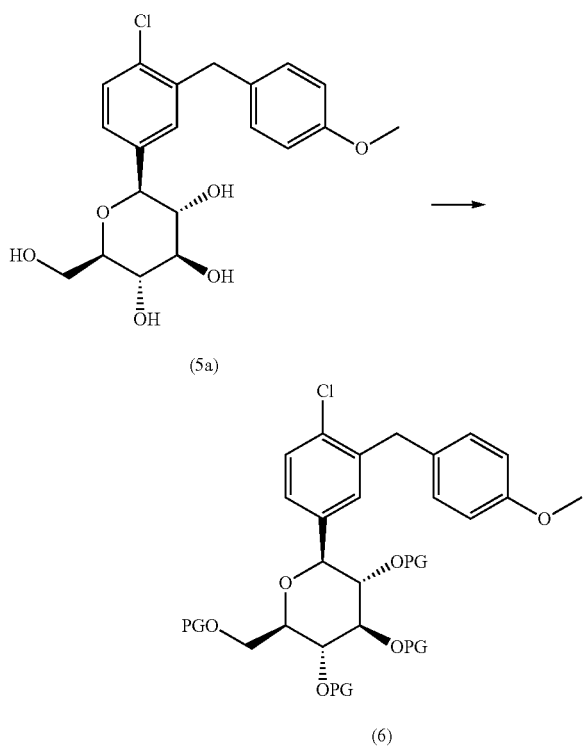

(e) subjecting compound (6) to O-demethylation in the presence of a suitable solvent and a reagent-pair, wherein PG and $R_1$ are as defined hereinbefore.

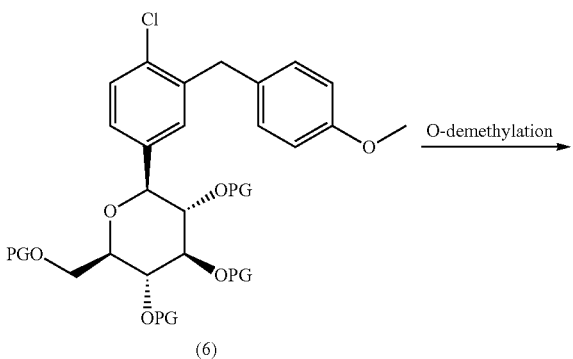

Wherein in step (a) reduction may be conducted with a reducing agent in the presence of or without a Lewis acid or suitable Bronsted acids such as hydrochloric acid, toluenesulfonic acid, trifluoroacetic acid or acetic acid.

The reaction may be carried out in a solvent at temperature ranging between 60-75° C. The solvent is preferably selected in view of the reducing agent and the optional Lewis acid. In preferred embodiments, step (a) is performed using sodium borohydride in the presence of aluminum chloride in tetrahydrofuran.

In the present context, compound (1) used in step (a) may be prepared according to the methods known in the art.

In step (b), the alkyl lithium may be selected from n-, sec-, and tert-butyl lithium, preferably n-butyl lithium is used. Examples for acid include without limitation, methanesulfonic acid, toluenesulfonic acid, hydrochloric acid, sulphuric acid, acetic acid, ammonium chloride and the like. The reaction may be carried out at temperature ranging between 100-120° C.

The compound (3) may be obtained from commercially available sources or prepared according to methods known in the literature.

In steps (c.1) and (d.2), reaction may be carried out in the presence of a suitable reagent for introducing the hydroxyl protecting group. In preferred embodiments, compound (4) and compound (5a) is treated with acetic anhydride in the presence of N,N-dimethylaminopyridine (DMAP) and dichloromethane. This step may be carried out at a temperature of about 20-30° C.

In steps (c.2) and (d.1), the reduction may be carried out using a reducing agent mentioned as hereinafter. In preferred embodiments, reduction is carried out using triethylsilane in the presence of boron trifluoride etherate in dichloromethane.

In step (e), thiourea and aluminium chloride ($AlCl_3$) form together a reagent pair. In thiourea/$AlCl_3$ reagent pair, the sulphur atom acts as a weak nucleophile and is capable of cleaving a methyl group from a methoxy, similar to the $AlCl_3$/Triethylsilane reagent.

Demethylation step may be carried out using a suitable reagent known in the art such as hydrogen bromide, boron tribromide, thiols such as dodecanethiol, decanethiol, cyclohexane thiol, cyclopentane thiol, cyclobutane thiol, thiophenol, methanethiol, ethanethiol, 1-propanethiol, 2-propanethiol, n-butanethiol, tertbutanethiol, furan-2-yl methanethiol, ethanedithiol, 1,2-propanedithiol, 1,3-propanedithiol, 1,3-butanedithiol, 1,4-butanedithiol in the presence of a suitable solvent to yield a compound (7). The choice of solvent depends on the type of reagent used.

Surprisingly the present inventors have found that O-demethylation using dodecanethiol and thiourea-aluminium chloride reagent pair in dichloromethane resulted in the desired compound with higher purity and better yields compared to dodecanethiol or any other thiol reagent which when used alone. The reagent pair is found to be advantageous when compared to hydrogen bromide or boron tribromide.

In one preferred embodiment, where PG is a hydroxyl protecting group preferably acetyl, compound (6) is subjected to hydrolysis to first cleave the hydroxyl protecting groups, followed by cleaving the phenolic methyl ether to yield the compound (7), wherein $R_1$ is hydrogen.

In another preferred embodiment, where PG is a hydroxyl protecting group preferably acetyl, compound (6) is subjected to O-demethylation using thiourea-$AlCl_3$ and dodecanethiol in dichloromethane to form compound (7), wherein $R_1$ is hydroxyl protecting group, preferably an acetyl group.

In one preferred embodiment, the process for preparing the compound (7) useful as a common intermediate for preparing empagliflozin as well as dapagliflozin, is described in scheme B.

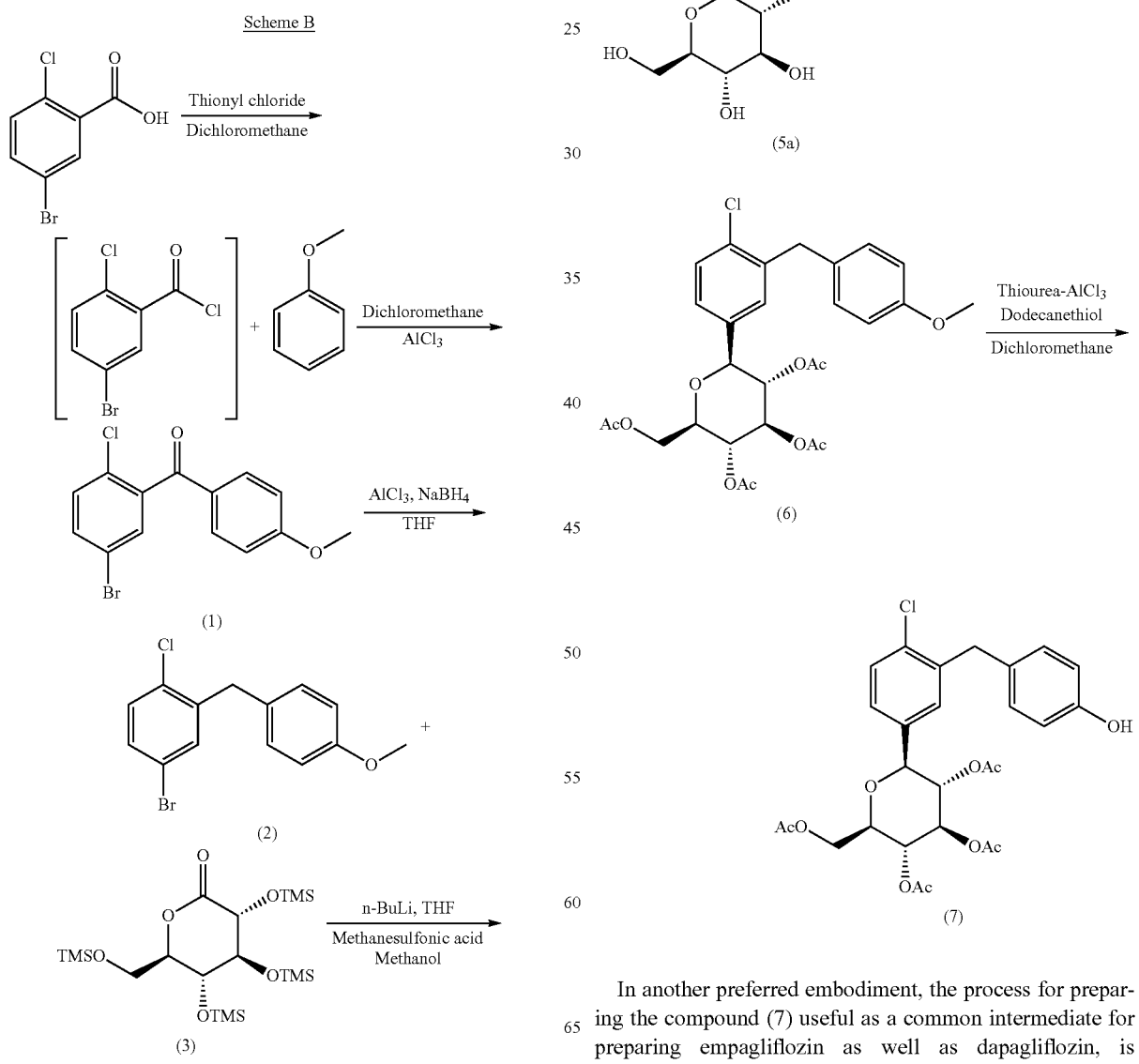

In another preferred embodiment, the process for preparing the compound (7) useful as a common intermediate for preparing empagliflozin as well as dapagliflozin, is described in the following scheme C.

Scheme C

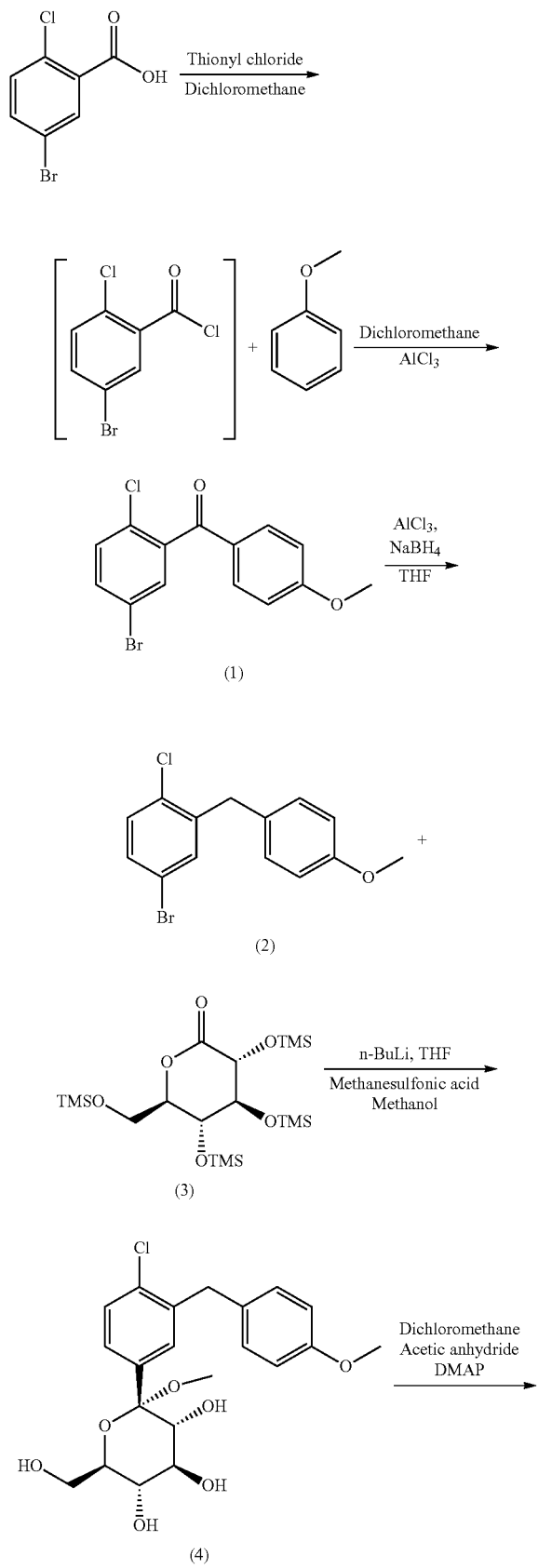

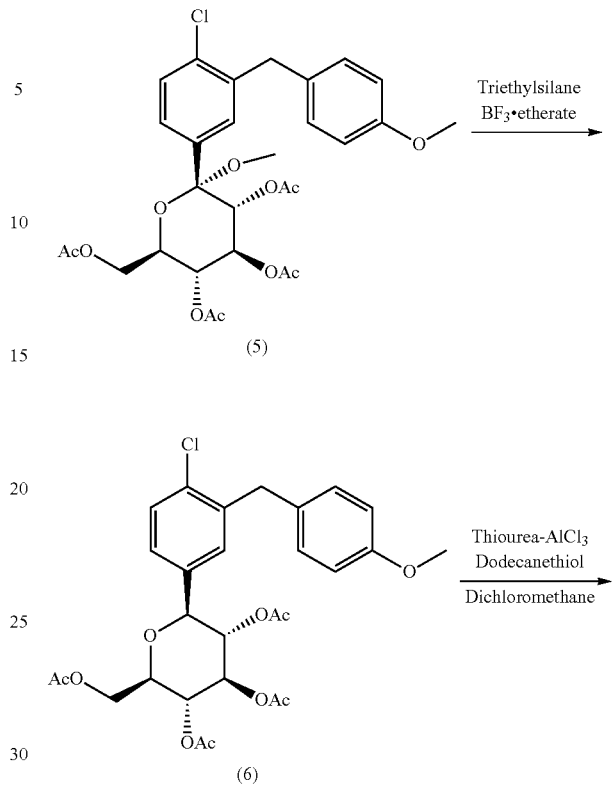

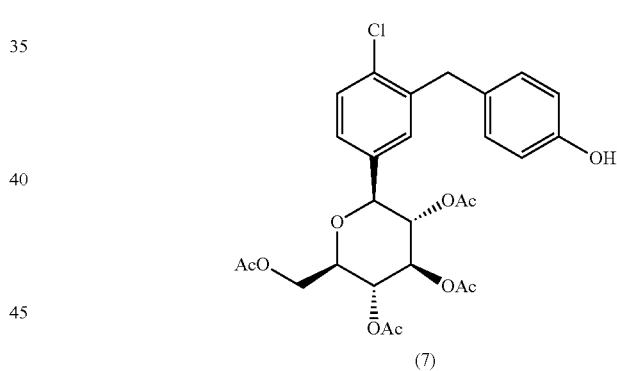

In a fifth embodiment, the present invention provides a novel process for preparing compound 8, where $R_2$ is selected from trifluoromethyl, $C_{1-6}$ alkyl, or an aryl group optionally substituted at para position with groups such as halogen, $C_{1-6}$ alkyl and $R_3$ is (R)-tetrahydrofuran-3-yl. The novel process of the present invention for preparing compound (8) may be represented in Scheme D.

Scheme D

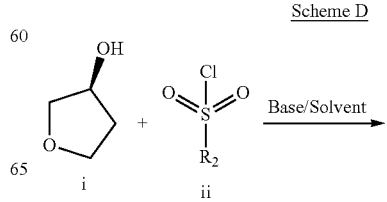

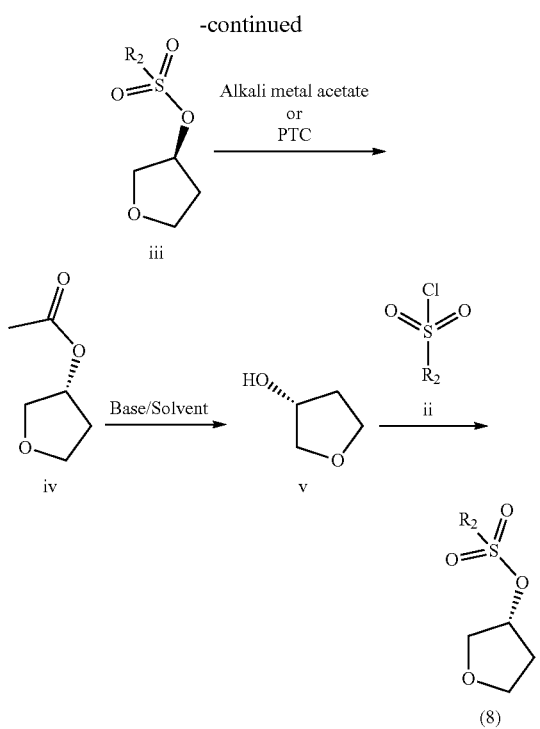

According to Scheme-D, (S)-3-hydroxytetrahydrofuran (i) is treated with an alkyl or aryl sulfonyl chloride compound (ii), wherein $R_2$ is selected from $C_{1-6}$ alkyl, trifluoromethyl or an aryl group optionally substituted at para position with groups such as halogen, nitro, $C_{1-6}$ alkyl, in the presence of a base to give a compound (iii), which is reacted with alkali metal acetate such as lithium acetate, sodium acetate, potassium acetate or cesium acetate, optionally in the presence of a phase transfer catalyst to obtain a compound (iv). Suitable phase transfer catalysts (PTC) include crown ethers such as 12-crown-4, 15-crown-5 or 18-crown-6. In preferred embodiments potassium acetate is used.

Further, the compound (iv) is subjected to hydrolysis in the presence of a base to yield (R)-3-hydroxytetrahydrofuran (v), which is further treated with compound (ii) wherein $R_2$ is selected from $C_{1-6}$ alkyl, trifluoro-methyl or an aryl group optionally substituted at para position with groups such as halogen, $C_{1-6}$ alkyl to obtain the compound (8) in desired configuration. The compound (8) is further reacted with compound (7) as described hereinbefore to yield empagliflozin in high yields and purity.

In an embodiment, the Lewis acid wherever used in the above mentioned reaction schemes may be selected from aluminum chloride, boron trifluoride etherate, copper (II) triflate, iron (III) chloride, tin (II) chloride, tin tetrachloride, zinc chloride, zinc iodide, indium (III) chloride, scandium triflate, trimethylsilyl triflate, trifluoroacetic acid and the like. Lewis acids may be used in stoichiometric or excess quantities.

The solvent(s) wherever used in the reaction(s) or processes of the present invention may be selected from hydrocarbon solvents such as n-hexane, n-heptane, cyclohexane, toluene, pentane, cycloheptane, methylcyclohexane, ethyl benzene or o-, m- or p-xylenes and the like; ether solvents such as 1,2-dimethoxyethane, tetrahydrofuran, 1,4-dioxane, diethyl ether, ethylene glycol dimethyl ether, ethylene glycol diethyl ether, diethylene glycol dimethyl ether, diethylene glycol diethyl ether, triethylene glycol dimethyl ether, t-butyl methyl ether or diisopropyl ether and the like; ester solvents such as ethyl formate, methyl acetate, ethyl acetate, isopropyl acetate, n-butyl acetate, t-butyl acetate, isobutyl acetate and the like; polar aprotic solvents such as N,N-dimethylacetamide (DMA), N,N-dimethylformamide (DMF), dimethylsulfoxide (DMSO), N-methylpyrrolidone (NMP) and the like; chlorinated solvents such as dichloromethane, chloroform and the like; ketone solvents such as acetone, methyl ethyl ketone, 2-pentanone, 3-pentanone, methyl butyl ketone, methyl isobutyl ketone and the like; nitrile solvents such as acetonitrile and the like; alcoholic solvents such as methanol, ethanol, n-propanol, isopropanol, n-butanol, isobutanol, t-butanol, 2-fluoroethanol, 2,2,2-trifluoroethanol, ethylene glycol, 2-methoxyethanol, 2-ethoxyethanol, diethylene glycol, diethylene glycol mono methyl ether, cyclohexanol and the like; polar protic solvents such as water or mixtures thereof.

The base(s) wherever used in the processes of the present invention may be selected from inorganic bases like alkali metal hydroxides such as lithium hydroxide, sodium hydroxide, potassium hydroxide and the like; alkali metal carbonates such as sodium carbonate, potassium carbonate, lithium carbonate and the like; alkali metal bicarbonates such as sodium bicarbonate, potassium bicarbonate, lithium bicarbonate and the like and ammonia, organic bases like alkali metal alkoxides such as sodium methoxide, sodium ethoxide, sodium tertbutoxide, potassium tert-butoxide and the like; triethylamine, methylamine, ethylamine, 1,5-diazabicyclo(4.3.0)non-5-ene (DBN), 1,8-diazabicyclo[5.4.0]undec-7-ene (DBU), 1,4-diazabicyclo[2.2.2]octane (DABCO), diisopropylamine, diisopropylethylamine, N-methylmorpholine, N-ethylmorpholine, piperidine, N,N-dimethylaminopyridine, pyridine, 2,6-lutidine, 2,4,6-collidine, 1-methylimidazole, 1,2,4-triazole or mixtures thereof.

Reduction or exhaustive reduction wherever performed in the above mentioned reaction schemes may be carried out using reducing agents selected from silanes such as triethylsilane, tripropylsilane, triisopropylsilane or diphenylsilane, sodium borohydride, sodium cyanoborohydride, zinc borohydride, borane complexes, lithium aluminum hydride, diisobutylaluminum hydride, vitride and the like.

In one embodiment, each compound obtained in each of the abovementioned reaction schemes may be proceeded to further steps without isolation and with or without drying in case if the compound is isolated.

In another embodiment, each compound obtained in each of the above-mentioned reaction schemes may be isolated and purified from the reaction mixture by, for example, cooling the reaction mixture, applying an isolation operation of filtration, concentration, extraction and the like to separate a crude reaction product, and applying a general purification operation such as column chromatography, recrystallization and the like.

According to the present invention, the industrially viable novel processes yields amorphous empagliflozin as such or by converting the crude compound obtainable from the said processes to a stable amorphous form by techniques known in the art.

The crude compound obtained from the improved process of the present invention may be purified by dissolution in one or more solvents, followed by addition of an anti-solvent to form a precipitate, followed by removing the solvent to give the amorphous compound.

Suitable techniques that may be used for the removal of solvent include but are not limited to rotational distillation using a device such as rotary evaporator, spray drying, filtration, agitated thin film drying (ATFD), freeze drying (lyophilization) and the like, optionally under reduced pressure.

The resulting solid may be collected by using techniques such as by scraping, or by shaking the container, or other techniques specific to the equipment used. The isolated solid may be optionally further dried to afford pure amorphous form of empagliflozin.

Drying may be suitably carried out using an air tray dryer, vacuum tray dryer, fluidized bed dryer, spin flash dryer, flash dryer, and the like. The drying may be carried out at atmospheric pressure or under reduced pressures, specifically at temperatures less than about 80° C. and more specifically less than about 60° C. The drying may be carried out for any time period required for obtaining a desired product quality, such as from about 30 minutes to about 24 hours, or longer. The dried product may optionally be subjected to a particle size reduction procedure to produce desired particle sizes and distributions. Milling or micronization may be performed after the completion of drying of the product. Equipment that may be used for particle size reduction includes but not limited to ball mill, roller mill, hammer mill, and jet mill.

In one embodiment, the present invention provides a process for the preparation of amorphous empagliflozin comprising: a) dissolving crude empagliflozin in a suitable solvent or mixtures thereof; b) optionally filtering the undissolved particles; c) removing the solvent by a suitable technique as described hereinbefore; and/or d) drying the solid at suitable temperature. The solvent(s) may be selected from any of the solvents described as hereinbefore.

The present invention provides amorphous empagliflozin characterized by a purity of about 99% or more by HPLC, free of any residual solvents, stable for 12 months on storage at 5±3° C.

In one embodiment, the process of the present invention provides substantially amorphous empagliflozin characterized by a purity of about 99% or more by HPLC, containing less than 1% of any crystalline form.

In preferred embodiments, the process of the present invention provides substantially amorphous empagliflozin characterized by a purity of about 99.5% or more by HPLC, containing less than 0.5% of any crystalline form.

In more preferred embodiments, the process of the present invention provides substantially amorphous empagliflozin characterized by a purity of about 99.7% or more by HPLC, with no detectable amount of any crystalline form.

In most preferred embodiments, the process of the present invention provides substantially amorphous empagliflozin characterized by a purity of about 99.89% by HPLC, with no detectable amount of any crystalline form, free of any residual solvents, stable for 12 months on storage at 5±3° C.

The present invention also provides stable amorphous solid dispersions/solutions of empagliflozin with pharmaceutically acceptable polymers, having a suitable polymorphic and chemical stability profile on storage at 25±2° C. and a relative humidity of 60±5%.

Examples of water soluble polymers include polyvinyl pyrrolidone (povidone), copovidone, polyvinyl alcohol, hydroxypropyl methylcellulose (hypromellose), hydroxypropyl cellulose, polyethylene glycol, polyvinyl caprolactam-polyvinyl acetate-polyethylene glycol copolymers (Soluplus™), and the like. Examples of water insoluble polymers include methylcellulose, ethylcellulose, polymethacrylates, hypromellose phthalate, hypromellose succinate, hypromellose acetate succinate (HPMC AS), cellulose acetate phthalate, carboxymethyl ethyl cellulose, and the like.

The ratio of empagliflozin prepared by the process of the present invention to the amount of polymer within the amorphous solid dispersion may be from about 1:1 to about 1:10 (w/w).

According to the present invention, the amorphous dispersions of empagliflozin may be prepared by a process comprising: (a) dissolving empagliflozin and a pharmaceutically acceptable polymer in a suitable solvent or mixtures thereof; (b) optionally filtering the un-dissolved particles; (c) removing the solvent by a suitable technique as described hereinbefore; (d) isolating amorphous solid dispersion of empagliflozin with a pharmaceutically acceptable polymer and (e) drying the amorphous solid dispersion of empagliflozin.

Isolation of amorphous solid dispersion of empagliflozin may involve one or more methods including removal of solvent by techniques known in the art e.g. evaporation, distillation, filtration of precipitated solid and the like, cooling, concentrating the reaction mass (RM), and the like. Stirring or other alternate methods such as shaking, agitation, and the like, may also be employed for the isolation.

In one embodiment, the present invention provides an amorphous solid dispersion comprising empagliflozin and ethyl cellulose, prepared by dissolving empagliflozin and ethyl cellulose in one or more solvents, followed by stirring to form a solution, optionally heating if a suspension is formed to obtain a clear solution. Removing the solvent by distillation under reduced pressure to give a residue, which may be further dried to yield amorphous dispersion of empagliflozin with ethyl cellulose.

In one preferred embodiment, the present invention provides an amorphous solid dispersion comprising empagliflozin and ethyl cellulose characterized by a purity of about 99% or more by HPLC, free of any residual solvents, stable for 6 months on storage at 25±2° C. and a relative humidity of 60±5%.

In more preferred embodiments, the present invention provides an amorphous solid dispersion comprising empagliflozin and ethyl cellulose characterized by a purity of about 99.5% or more by HPLC, free of any residual solvents, stable for 6 months on storage at 25±2° C. and a relative humidity of 60±5%.

In most preferred embodiments, the present invention provides an amorphous solid dispersion comprising empagliflozin and ethyl cellulose characterized by a purity of about 99.89% by HPLC, free of any residual solvents, stable for 6 months on storage at 25±2° C. and a relative humidity of 60±5%.

In one embodiment, the present invention provides an amorphous solid dispersion comprising empagliflozin and hydroxypropyl cellulose (HPC), prepared by dissolving empagliflozin and hydroxypropyl cellulose in one or more solvents, followed by stirring to form a solution, optionally heating if a suspension is formed to obtain a clear solution. Removing the solvent by distillation under reduced pressure to give a residue, which may be further dried to yield amorphous dispersion of empagliflozin with HPC.

In one preferred embodiment is provided an amorphous solid dispersion comprising empagliflozin and hydroxyl propyl cellulose characterized by a purity of about 99% or more by HPLC, free of any residual solvents.

In more preferred embodiments, the present invention provides an amorphous solid dispersion comprising empagliflozin and hydroxyl propyl cellulose characterized by a purity of about 99.5% or more by HPLC, free of any residual solvents.

In most preferred embodiments, the present invention provides an amorphous solid dispersion comprising empagliflozin and hydroxyl propyl cellulose characterized by a purity of about 99.78% by HPLC, free of any residual solvents.

In one embodiment, the products obtained from the processes of the present invention may be used for preparation of pharmaceutical formulations useful for the prevention and/or treatment of diseases and conditions associated with SGLT-2 inhibition.

Methods:
1. High Performance Liquid Chromatography (HPLC):
(a) (1S)-1,5-anhydro-1-C-[4-chloro-3-[[4-[[(3S)-tetrahydro-3-furanyl]oxy]phenyl]methyl]phenyl]-D-glucitol, i.e., empagliflozin (amorphous)
  Apparatus: A liquid chromatographic system is to be equipped with variable
  wavelength UV-Detector and Integrator.
  Column: Promosil C18, 250×4.6 mm, 100 A°, 5 µm or equivalent
  Column Temperature: 40° C.
  Wavelength: 225 nm
  Flow rate: 1.2 mL/min
  Injection volume: 5 µL
  Run Time: 60 min
  Elution: Gradient
  Diluent: Acetonitrile: Water (50:50 v/v)
  Mobile phase A: Buffer solution
  Mobile phase B: Acetonitrile: Water (95:5 v/v)
  Buffer solution: Transfer accurately about 1 mL of ortho phosphoric acid into 1000 mL of milli-Q water, filter through 0.45 µm nylon membrane and sonicate to degas.
(b) Amorphous solid dispersion of empagliflozin and ethyl cellulose (EC)
  Chromatographic conditions are same as given under (a).
(c) Amorphous solid dispersion of empagliflozin and hydroxypropyl cellulose (HPC)
  Chromatographic conditions are same as given under (a), except for:
  Wavelength: 220 nm
  Column temperature: 35° C.
  Mobile Phase B: Acetonitrile: Water (90:10 v/v)
(d) (1S)-1,5-anhydro-1-C-[4-chloro-3-[(4-ethoxyphenyl) methyl] phenyl]-D-glucitol i.e., dapagliflozin
  Chromatographic conditions are same as given under (a), except for:
  Column temperature: 35° C.
  Run Time: 55 min
  Mobile Phase B: Acetonitrile: Water (90:10 v/v)
2. Powder X-ray Diffraction (PXRD):
  The diffraction patterns were measured using Bruker D2 PHASER diffractometer equipped with LYNXEYE™ detector, used radiation Cu Kα (λ=1.54060 Å), excitation voltage: 30 kV, anode current: 10 mA, measured range: 3-40° 2θ, increment: 0.01° 2θ.

TABLE NO. 1

Chemical Purity of Empagliflozin

| Stability Period (Temp = 5 ± 3° C.) | Chemical Purity (HPLC) | PXRD |
|---|---|---|
| Initial | 99.88 | Amorphous |
| 1 month | 99.90 | Amorphous |
| 3 months | 99.88 | Amorphous |
| 6 months | 99.89 | Amorphous |
| 12 months | 99.88 | Amorphous |

TABLE NO. 2

Chemical Purity of Solid Dispersions of Empagliflozin with Ethyl Cellulose and HPC

| Stability Period Temp = 25 ± 2° C., RH = 60 ± 5% | Empagliflozin-Ethyl Cellulose Dispersion | | Empagliflozin-HPC Dispersion | |
|---|---|---|---|---|
| | Chemical Purity (HPLC) | PXRD | Chemical Purity (HPLC) | PXRD |
| Initial | 99.89 | Amorphous | 99.78 | Amorphous |
| 1 month | 99.89 | Amorphous | 99.76 | Amorphous |
| 3 months | 99.88 | Amorphous | 99.77 | Amorphous |
| 6 months | 99.86 | Amorphous | 99.77 | Amorphous |

Advantages of Present Invention

1. Use of anisole in the preparation of compound (1), which is further used for preparing empagliflozin and dapagliflozin reduces cost and provides better yields and purities when compared with the use of fluorobenzene (for empagliflozin) and phenetole (for dapagliflozin) as observed in the prior art.
2. Use of Lewis acid such as $TiCl_4$ in the conversion of compound (1) to compound (2) is known in the art. Titanium tetrachloride ($TiCl_4$) is a strong Lewis acid, exothermically forming adducts with even weak bases such as THF and explosively with water and releasing HCl. However, the present invention uses aluminium chloride which is better, cheaper and safer Lewis acid when compared to titanium tetrachloride as used in the prior art.
3. O-demethylation using dodecanethiol and thiourea-aluminium chloride reagent pair provides the desired compound with higher purity and better yields compared to dodecanethiol or any other thiol reagent when used alone. The reagent pair method is advantageous when compared to boron tribromide as well as HBr.
4. Present invention provides a common intermediate (7) for both empagliflozin and dapagliflozin synthesis which is cost effective and the synthesis of the said products becomes highly convergent as opposed to the linear synthetic schemes employed in the prior art.
5. Present inventors surprisingly provide a simplified, cheaper process for preparation of (R)-3-hydroxytetrahydrofuran, which is otherwise expensive from a less expensive, commercially available (S)-3-hydroxy tetrahydrofuran.

TABLE NO. 3

Comparison of Prior Art Process and Present Invention

| | | Prior art | Present invention | Observation |
|---|---|---|---|---|
| Compound (1) | Reagent | Oxalyl chloride | Thionyl Chloride | Thionyl chloride is cheaper and safer chlorinating reagent than oxalyl chloride which is otherwise highly toxic |
| | Yield | 64% | 81% | |

TABLE NO. 3-continued

Comparison of Prior Art Process and Present Invention

|  |  | Prior art | Present invention | Observation |
|---|---|---|---|---|
| Compound (2) | Reagent | Et$_3$SiH/BF$_3$·Et$_2$O (or) TiCl$_4$ | AlCl$_3$/NaBH$_4$ | Triethylsilane and boron trifluoride etherate are expensive and required in much larger quantities and titanium tetrachloride reacts explosively with water to release HCl. |
|  | Yield | 61% | 75% |  |
| Compound (7) | Reagent | BBr$_3$, HBr in acetic acid | Dodecanethiol, AlCl$_3$, Thiourea | BBr$_3$ is expensive; with HBr, reaction doesn't complete. |
|  | Yield | 65% | 92% |  |
|  | Purity | 80% | 98.65% |  |

Further the novel processes for preparing the SGLT-2 inhibitors and novel intermediates thereof, according to the present invention are illustrated in the following examples. The following specific and non-limiting examples are to be construed as merely illustrative, and do not limit the present disclosure in any way whatsoever.

EXAMPLES

Example 1: General procedure to prepare (3R,4S, 5R,6R)-6-(acyloxymethyl)-2-(4-chlorophenyl)-2-methoxytetrahydro-2H-pyran-3,4,5-triyl triacylate (IV)

To a solution of 40 mmol of (3R,4S,5S,6R)-2-(4-chlorophenyl)-6-(hydroxymethyl)-2-methoxytetrahydro-2H-pyran-3,4,5-triol in toluene (120 ml), DMAP (0.4 mmol), diisopropylethylamine (165 mmol), and acyl anhydride or acyl halide (170 mmol) were added sequentially under nitrogen atmosphere at ambient temperature. After stirring for 6 h the reaction was complete by HPLC. 1N H$_3$PO$_4$ solution was added to the reaction mixture to neutralize to pH 6.5-7 and the aqueous layer was extracted further with EtOAc (100 mL). The organic extracts were combined and washed with brine (50 mL), dried (Na$_2$SO$_4$), and filtered. The filtrate was evaporated to obtain the product as a semi solid.

Example 2: General procedure to prepare (2R,3R, 4R,5S,6S)-2-(acyloxymethyl)-6-(4-chlorophenyl) tetrahydro-2H-pyran-3,4,5-triyl triacylate (V)

A solution of (3R,4S,5R,6R)-6-(acyloxymethyl)-2-(4-chlorophenyl)-2-methoxytetra hydro-2H-pyran-3,4,5-triyl triacylate from example 1 (34 mmol) in CH$_3$CN (170 mL) was prepared at room temperature (RT) under nitrogen atmosphere and 1 mol equivalent of water was added. The solution was cooled in an ice bath and Et$_3$SiH (109 mmol) was added. To this solution was added BF$_3$.Et$_2$O (82 mmol) over 30 min, and the mixture was allowed to warm to 15° C. over 20 min. Upon completion, the reaction was quenched with aqueous saturated NaHCO$_3$ (100 mL); the pH of the aqueous layer was 7. The organic layer was washed with brine (170 mL) and the solution was dried (Na$_2$SO$_4$). The solvent was evaporated to give the corresponding product as a white solid.

Example 3: General procedure to prepare (2R,3R, 4R,5S,6S)-2-(acyloxymethyl)-6-(4-chloro-3-(4-halo/alkyl or aryl sulfonato/triflato-benzoyl)phenyl)tetrahydro-2H-pyran-3,4,5-triyl triacylate (VI)

To a solution of 4-halo/alkyl or aryl sulfonato/triflato-benzoic acid (B) (36 mmol) in dichloromethane (80 ml) was added thionyl chloride (43 mmol) drop-wise at RT. The reaction mass (RM) was refluxed for 3 h. The solvent was distilled off completely under vacuum. Toluene (30 ml) was added to the reaction mass and distilled off toluene completely under vacuum to obtain corresponding acid chloride as a residue. Dichloromethane (50 ml) was added to the residue and cooled to 5° C. Anhydrous aluminium chloride (40 mmol) was added to the reaction mass in four portions under nitrogen atmosphere. A solution of (2R,3R,4R,5S,6S)-2-(acyloxymethyl)-6-(4-chlorophenyl)tetrahydro-2H-pyran-3,4,5-triyl triacylate obtained from example 2 (30 mmol) in dichloromethane (35 ml) was added drop-wise to the reaction mass at 5° C. The reaction mass was warmed to RT and stirred at RT for 3 h. The reaction mass was cooled to 5° C. and conc. hydrochloric acid (50 ml) was added and stirred at RT for 10 min. The organic layer was separated and washed successively with water (1×30 ml), 10% aq. sodium bicarbonate solution (2×30 ml) and brine (1×30 ml). The organic layer was dried over anhydrous sodium sulfate and the solvents distilled off under vacuum below 50° C. Methanol (50 ml) was added to the residue and stirred for 1 h at 50° C., cooled to 5° C. and filtered. The filtered solid was dried for 4 h at 40° C. to obtain the product as a white solid.

Example 4: General procedure to prepare (2R,3R, 4R,5S,6S)-2-(acyloxymethyl)-6-(4-chloro-3-(4-(((S)-tetrahydrofuran-3-yl) oxy) benzoyl) phenyl) tetrahydro-2H-pyran-3,4,5-triyl triacylate (VIIa)

To a solution of (2R,3R,4R,5S,6S)-2-(acyloxymethyl)-6-(4-chloro-3-(4-halo/alkyl or aryl sulfonato/triflato-benzoyl) phenyl) tetrahydro-2H-pyran-3,4,5-triyl triacylate obtained from example 3 (12 mmol) and (S)-3-hydroxytetrahydrofuran (C) (12 mmol) in tetrahydrofuran (25 ml) was added solid potassium tert-butoxide (15 mmol) in several portions under nitrogen atmosphere. The reaction mass was refluxed for 8 h, pH adjusted to 7 using dilute hydrochloric acid. The reaction mass was filtered, the volatiles were distilled off. The residue was dissolved in dichloromethane (50 ml) and washed with water (2×25 ml) and brine (1×25 ml). The solution was dried over anhydrous sodium sulfate and evaporated to yield the product as a solid.

Example 5: General Procedure to Prepare (2-chloro-5-((2S,3R,4R,5S,6R)-3,4,5-trihydroxy-6-(hydroxymethyl) tetrahydro-2H-pyran-2-yl) phenyl) (4-(((S)-tetra hydrofuran-3-yl)oxy)phenyl) methanone (VII)

(2R,3R,4R,5S,6S)-2-(acyloxymethyl)-6-(4-chloro-3-(4-(((S)-tetrahydrofuran-3-yl) oxy) benzoyl) phenyl) tetrahydro-2H-pyran-3,4,5-triyl triacylate (9 mmol), obtained from example 4, was dissolved in methanol (25 mL) containing NaOH (9.9 mmol) and stirred at RT for 8 h. Methanol was distilled completely under vacuum and the residue was diluted with dichloromethane (30 mL). The organic layer was washed with water (2×25 mL) and the organic layer was dried over anhydrous sodium sulfate and the solvent was removed under vacuum to obtain the title compound.

Example 6: General Procedure a (Exhaustive Reduction) to Prepare Empagliflozin (VIII)

To a suspension of aluminium chloride (80 mmol) in THF (60 ml) pre-cooled to 10° C., was added sodium borohydride (320 mmol) in 5 portions under a nitrogen atmosphere. The reaction mass was stirred at RT for 2 h. A solution of (2R,3R,4R,5S,6S)-2-(acyloxymethyl)-6-(4-chloro-3-(4-(((S)-tetrahydrofuran-3-yl)oxy)benzoyl)phenyl)tetra hydro-2H-pyran-3,4,5-triyl triacylate obtained from example 4 (10 mmol) in THF (25 ml) was added to the reaction mass drop-wise and temperature rose up to 50° C. The reaction mass was refluxed for 36 h. The reaction mass was cooled to 10° C. and 10% hydrochloric acid (50 ml) was added drop-wise. The reaction mass was stirred at RT for 1 h. Ethyl acetate (50 ml) was added and stirred at RT for 15 min. Organic layer was separated and the aqueous layer was extracted with ethyl acetate (2×25 ml). The combined organic layers were dried over anhydrous sodium sulfate, filtered and the solvent distilled off completely under vacuum to obtain the crude product which was chromatographed on silica gel (60-120 mesh) beginning 5% methanol in dichloromethane and gradually increased the polarity to 50% methanol in dichloromethane. The product fractions were distilled off under vacuum at 45° C. to obtain empagliflozin in amorphous form.

Example 7: General Procedure B (Carbonyl Reduction) to Prepare Empagliflozin (VIII)

A solution of (2-chloro-5-((2S,3R,4R,5S,6R)-3,4,5-trihydroxy-6-(hydroxymethyl)tetra hydro-2H-pyran-2-yl) phenyl) (4-(((S)-tetrahydrofuran-3-yl) oxy) phenyl) methanone from example 5 (10 mmol) in $CH_3CN$ (60 mL) was prepared at room temperature under nitrogen atmosphere and 1 mol equivalent of water was added. The solution was cooled in an ice bath and $Et_3SiH$ (36 mmol) was added. To this solution was added $BF_3.Et_2O$ (28 mmol) over 30 min, and the mixture was allowed to warm to 15° C. over 20 min. Upon completion, the reaction was quenched with aqueous saturated $NaHCO_3$ (35 mL); the pH of the aqueous layer was 7. The organic layer was washed with brine (60 mL) and the solution was dried ($Na_2SO_4$). The mixture was filtered and the solvent was evaporated to obtain the crude product which was chromatographed on silica gel (60-120 mesh) beginning 5% acetonitrile in dichloromethane and gradually increased the polarity to 50% acetonitrile in dichloromethane. The product fractions were distilled off under vacuum at 45° C. to obtain empagliflozin in amorphous form.

Example 8: Preparation of (5-bromo-2-chlorophenyl)(4-methoxyphenyl) methanone (1)

A solution of 5-bromo-2-chloro benzoic acid (150 g) in dichloromethane (750 mL) was stirred for 15-30 min. Dimethylformamide (0.6 ml) and thionyl chloride (138.7 mL) was charged to the above reaction mass (RM), stirred for 10-15 min. The RM was heated to 40-45° C. and maintained for 2 h. After completion of reaction, distilled the RM completely under vacuum at 45° C. Charged dichloromethane (1200 mL) in to the mass, cooled to 0-5° C. Charged aluminum chloride (101.9 g) into the RBF, slowly added anisole (74.2 g) into the mass at same temperature. After the reaction is complete, water (750 mL) was added to the RM, and slightly warmed to 20-30° C. The organic and aqueous layers were separated, the aqueous layer was extracted with dichloromethane (2×750 mL). Then the organic layer was washed with 2N hydrochloric acid solution, dichloromethane (2×750 mL), followed by washing with sodium bicarbonate (2×750 mL). The organic layer was then washed with sodium chloride solution (750 mL) and dried over sodium sulfate. Then distilled the organic layer completely under vacuum at 40° C. to remove the solvent completely. The solid obtained was washed with methanol (300 mL), cooled to 0-5° C. and stirred for 60 min to obtain a precipitate. Filtered the mass and the compound was washed with 100 mL of chilled (about 10° C.) methanol. Then air dried the compound for 6 h to obtain the title compound (168.5 g, 81.24%). (Purity by HPLC: 99.22%).

Example 9: Preparation of 2-(4-methoxybenzyl)-4-bromo-1-chlorobenzene (2)

A solution of compound 1 (50 g) from Example 8 and tetrahydrofuran (100 mL) was stirred for 10 min. Cooled the RM to 0-5° C. Aluminum chloride (42.9 g) was charged to the RM at the same temperature, stirred for 30 min at 0-5° C. Sodium borohydride (18 g) was added to the RM, stirred for 60 min at 5-10° C. RM was heated to 65-70° C. and maintained for 15 h. After completion of reaction, the RM was cooled to 20-30° C. and then to 0-5° C. Slowly added water (500.0 mL) in to the mass at 5-10° C. Charged ethyl acetate (500 mL) to the RM and stirred for 10 min at 20-30° C. The aqueous and organic layers were separated, aq. layer was extracted with ethyl acetate (250 mL). Organic layer was washed with saturated sodium bicarbonate solution (2×250 mL). Combined organic layers were dried over sodium sulfate. The organic layer was distilled completely under vacuum at 40° C. and residue was treated with methanol (100 mL). Stirred and, cooled the mass to −5 to 0° C. and maintained for 60 min. Filtered the mass and compound was washed with 30 mL of chilled (about 10° C.) methanol. The compound was air dried for 6 h to obtain the title compound (36.2 g, 75.65%). (Purity by HPLC: 99.63%).

Example 10: Preparation of (2S, 3R, 4S, 5S, 6R)-2-(3-(4-methoxybenzyl)-4-chlorophenyl)-tetrahydro-6-(hydroxymethyl)-2-methoxy-2H-pyran-3,4,5-triol (4)

A mixture of toluene (300 mL) and 50 g of compound (2) from example 9 was heated to 110-115° C. and stirred for 90 min. Charged 113 g of protected lactone (3) (wherein PG=trimethylsilyl) and tetrahydrofuran (350 mL) in to the RM. Cooled the RM to −70 to −75° C. and slowly added n-butyl lithium (216 mL) to the RM at same temperature. After completion of reaction, slowly added 85.5 g of methane sulfonic acid in methanol solution (see the note below). Then the mass was warmed to 20-30° C. and stirred for 15 h. The pH of the RM was adjusted to 8.0 by using saturated sodium bicarbonate solution. Aqueous and organic layers were separated. The organic layer was distilled completely under vacuum at 50° C. After removal of solvent, ethyl acetate was added and stirred for 10 min. Aq and organic layers were separated and combined organic layers were washed with sat. Sodium chloride solution (200 mL). Organic layer dried with sodium sulfate and distilled the organic layer under vacuum at 50° C. to obtain a wet residue containing the title compound (4).

Note: Methane sulfonic acid solution was prepared by mixing 85.5 g of methane sulfonic acid in 250 ml of methanol.

Example 11: Preparation of Compound (5) (PG=Acetyl)

To the residue obtained from Example 10, was added dichloromethane (400 mL), followed by addition of N,N-dimethylaminopyridine (3.5 g) and acetic anhydride (82.3 g). The RM was stirred for 12 h at 20-30° C. After the completion of reaction, water (250 ml) was added to the RM and stirred for 10 min. Aqueous and organic layers were separated. The aqueous layer was extracted with dichloromethane (100 mL). Total organic layer were combined and 250 ml of 2N hydrochloric acid solution was added. Stirred the RM for 5 min. Layers were separated, followed by washing with water (250 mL) and stirred for 10 min. Combined organic layers were dried with 20 g of sodium sulfate. The organic layer was distilled completely under vacuum at 45° C. After distillation methanol (100 mL) was charged and distilled completely under vacuum, to obtain a residue containing the compound (5).

Example 12: Preparation of Compound (6)

To the residue obtained from Example 11 was added dichloromethane (250 mL) and acetonitrile (250 mL) in to the RB flask. The reaction mass was cooled to −60±5° C. and slowly added triethylsilane (35.5 g) at the same temperature and stirred for 5 min. Borontrifluoride etherate (52 g) was slowly added to the reaction mass at −60±5° C. Warmed the mass to 20-30° C. After completion of reaction, charged ethyl acetate (500 mL) in to the RM and stirred for 5 min. Aqueous and organic layers were separated and extracted with ethyl acetate (500 mL). Combined the total organic layers and dried over anhydrous sodium sulfate. Distilled the organic layer completely under vacuum at 55° C. followed by washing with methanol and removing the solvent to yield the compound (6) (36 g). (Purity by HPLC: 99.16%)

Example 13: Preparation of Compound (5a)

The compound 5a was prepared from compound 4 using the conditions and reagents as described under Example 12.

Example 14: Preparation of Compound (6) from Compound 5a

Compound 6 was prepared from compound 5a using the conditions and reagents described under Example 11.

Example 15: Preparation of Compound (7)

To compound 6 (2 g) obtained from example 12 or example 14, was added dichloromethane (15 mL), and cooled the mass to −5 to −10° C. Slowly added 20 mL of dodecanethiol & thiourea-AlCl3 to the reaction mass. After completion of reaction, water (50 mL) and dichloromethane (20 mL) was added at 0-5° C. Stirred and aqueous and organic layers were separated. The aqueous layer was extracted with dichloromethane. Combined organic layers were dried with anhydrous sodium sulfate after washing with water. The organic layer was distilled completely under vacuum at 40° C. and dried for 4 h to yield the title compound (1.8 g, 92.31%) (Purity by HPLC: 98.65%).

Example 16: Preparation of Compound (8) ($R_2$=phenyl; $R_3$=ethyl)

To a solution of ethanol (15.64 g, 0.34 mol) and triethylamine (0.4 mol) in THF (75 mL) at 10° C., was added alkyl or aryl sulfonyl chloride (0.4 mol) in three portions. The RM was stirred for 3 h at RT and diluted with hexanes (50 mL). The precipitated triethylamine hydrochloride was filtered and the filtrate was evaporated under vacuum to obtain compound (8) as a syrup which was taken to next step without further purification.

Example 17: Preparation of Compound (8) ($R_3$=(R)-tetrahydrofuran-3-yl)

(a) Preparation of Compound iii:
To a solution of (S)-3-hydroxytetrahydrofuran (30 g, 0.34 mol) and triethylamine (0.4 mol) in THF (150 mL) at 10° C., was added alkyl or aryl sulfonyl chloride (0.4 mol) in three portions. The RM was stirred for 3 h at RT and diluted with hexanes (75 mL). The precipitated triethylamine hydrochloride was filtered and the filtrate was evaporated under vacuum to obtain the corresponding sulfonate as a syrup which was taken to next step without further purification.

(b) Preparation of Compound iv:
Toluene (200 mL) was added to the residue obtained from step (a) followed by potassium acetate (0.4 mol) and 18-crown-6 (0.04 mol) and the RM was refluxed for 20 h. The RM was cooled to RT, water (100 mL) was added and stirred at RT for 30 min. The organic layer was separated, dried over anhydrous sodium sulfate and the solvent was distilled completely under vacuum to obtain (R)-3-acetoxytetrahydrofuran (iv) as an oil. This reaction can also be performed in the absence of 18-crown-6 without affecting yield and purity of the product.

(c) Preparation of Compound v:
The oil obtained from step (b) was dissolved in methanol (150 mL) containing sodium hydroxide (0.4 mol) at RT. The RM was stirred at RT for 4 h. The solvent was removed under vacuum and the residue was diluted with dichloromethane (150 mL). The organic layer was washed with water (2×100 mL) and the organic layer was dried over anhydrous sodium sulfate and the solvent was removed under vacuum to obtain (R)-3-hydroxy tetrahydrofuran as an oil which was purified by vacuum distillation (24 g, 80% overall)

(c) Preparation of Compound (8):
To a solution of (R)-3-hydroxytetrahydrofuran (20 g, 0.23 mol) from step (c) and triethylamine (0.27 mol) in THF (125 mL) at 10° C., was added alkyl or aryl sulfonyl chloride (0.27 mol) in three portions. The RM was stirred for 3 h at RT and diluted with hexanes (65 mL). The precipitated triethylamine hydrochloride was filtered and the filtrate was evaporated under vacuum to obtain compound (8) as a syrup which was taken to next step without further purification.

Example 18: Preparation of Empagliflozin (9a)

To Compound (7) (25 g), obtained from example 15, was charged acetonitrile (250 mL) in to the RB flask, followed by addition of potassium carbonate (25 g). The RM was stirred for 10 min at 20-30° C. Compound (8) (15 g), obtained from example 17, was charged to the RM, heated to 70-75° C. and stirred for 36 h. After completion of the reaction, the RM was cooled to 10-15° C. Slowly water (250 mL) was added followed by addition of ethyl acetate (250 mL), stirred for 10 min. The aqueous and organic layers were separated. The organic layer was dried over anhydrous sodium sulfate and the solvent was distilled under vacuum to obtain the crude product which was chromatographed on silica gel (60-120 mesh) beginning 5% methanol in dichloromethane and gradually increased the polarity to 50% methanol in dichloromethane. The product fractions were distilled off under vacuum at 45° C. to obtain empagliflozin in amorphous form. (15 g). (Purity by HPLC: 99.88%) (PXRD pattern: Amorphous)

Example 19: Preparation of Amorphous Solid Dispersion of Empagliflozin and Ethyl Cellulose To a solution of the product obtained from example 18 (2 g), in methanol (120 mL) was charged ethyl cellulose (4 g) at RT. The RM was stirred for 20 min at 45° C. Dichloromethane (60 mL) was charged to the RM and stirred for 10 min. The solvent was distilled completely under vacuum to give a wet residue, which upon drying for 30 min resulted in the title product as a solid. The product obtained was crushed using mortar-pestle.

Figure 2:
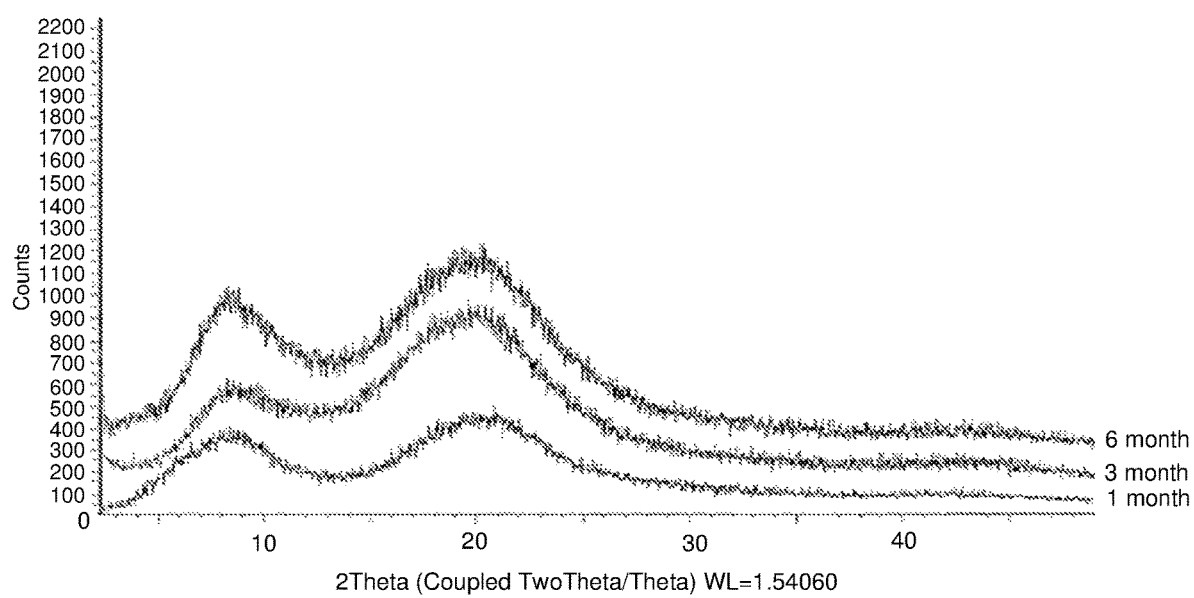
FIG. 2 represents an overlay of powder X-ray diffraction pattern of an amorphous solid dispersion comprising empagliflozin and ethyl cellulose at $1^{st}$, $3^{rd}$ and $6^{th}$ months.

The solid obtained was found to be amorphous from the PXRD pattern with no significant sharp peaks, as observed in FIG. 2.

Example 20: Preparation of Amorphous Solid Dispersion of Empagliflozin and Hydroxypropyl Cellulose (HPC)

To a solution of the product obtained from example 18 (2 g), in methanol (360 mL) was charged hydroxypropyl cellulose (4 g) at RT. The RM was stirred for 20 min at 45° C. Dichloromethane (360 mL) was charged to the RM and stirred for 10 min. The solvent was distilled completely under vacuum to give a wet residue, which upon drying for 30 min resulted in the title product as a solid. The product obtained was crushed using mortar-pestle.

Figure 3:
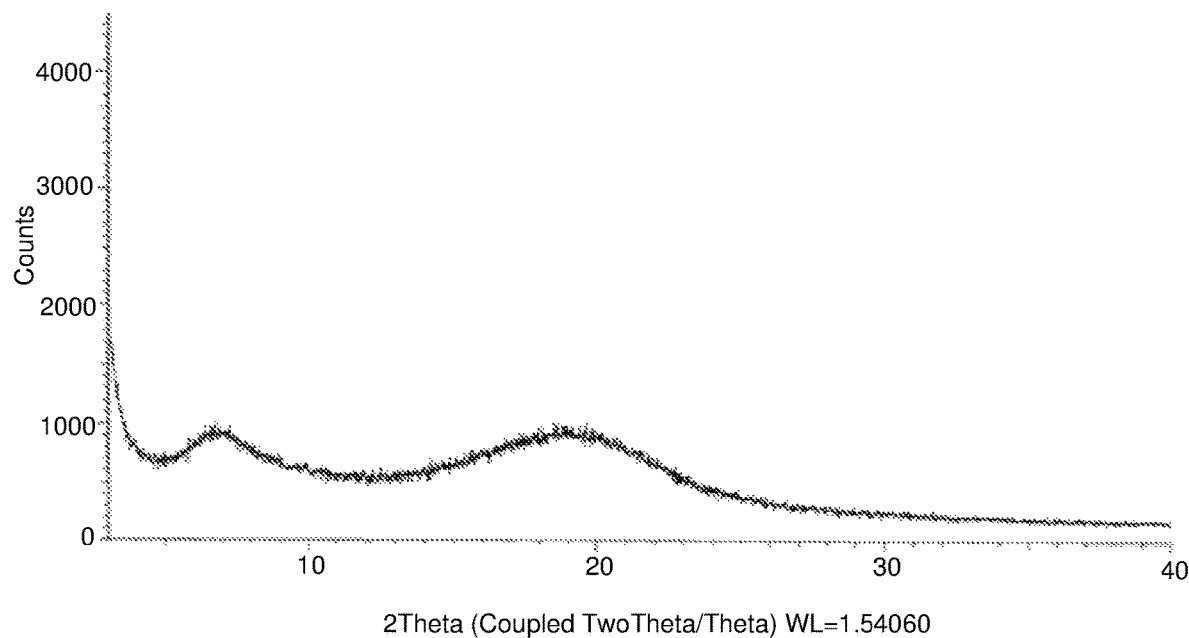
FIG. 3 represents powder X-ray diffraction pattern of an amorphous solid dispersion comprising empagliflozin and hydroxypropyl cellulose.

The solid obtained was found to be amorphous from the PXRD pattern with no significant sharp peaks, as observed in FIG. 3.

Example 21: Preparation of Dapagliflozin (9b)

To Compound (7) (25 g), obtained from example 15, was charged acetonitrile (250 mL) in to the RB flask, followed by addition of potassium carbonate (25 g). The RM was stirred for 10 min at 20-30° C. Compound (8) (10 g), obtained from example 16, was charged to the RM, heated to 70-75° C. and stirred for 36 h. After completion of the reaction, the RM was cooled to 10-15° C. Slowly water (250 mL) was added followed by addition of ethyl acetate (250 mL), stirred for 10 min. The aqueous and organic layers were separated.

The organic layer was dried over anhydrous sodium sulfate and the solvent was distilled under vacuum to obtain the product as a residue (22 g), (Purity by HPLC: 99.72%).

The above examples are merely illustrative, and do not limit the scope of the invention in anyway.

The foregoing embodiments and advantages are merely exemplary and are not to be construed as limiting the scope of the present invention. The description of the exemplary embodiments of the present invention is intended to be illustrative and not to limit the scope of the invention. Various modifications, alterations and variations, which are apparent to a person skilled in the art, are intended to fall within the scope of the invention.

We claim:

1. A process for the preparation of SGLT-2 inhibitors represented by a compound (9) comprising the steps of:

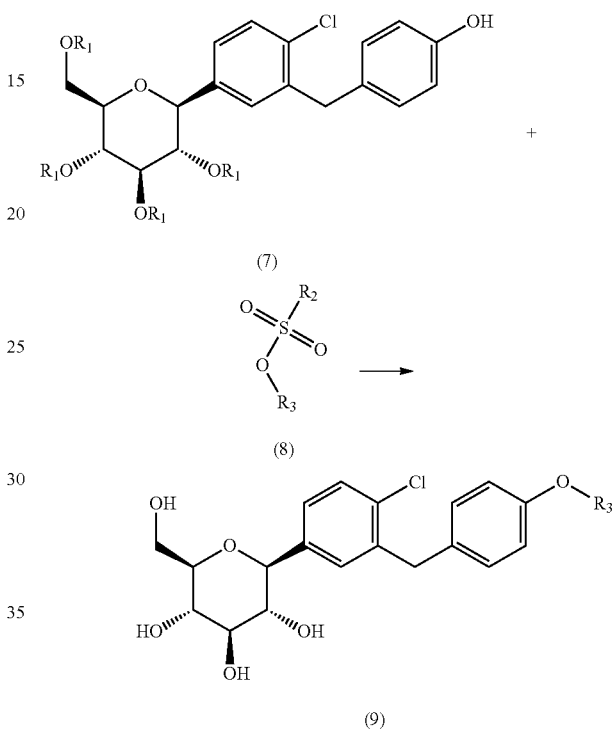

(a) reducing compound (1) to obtain a diphenylmethane compound (2);

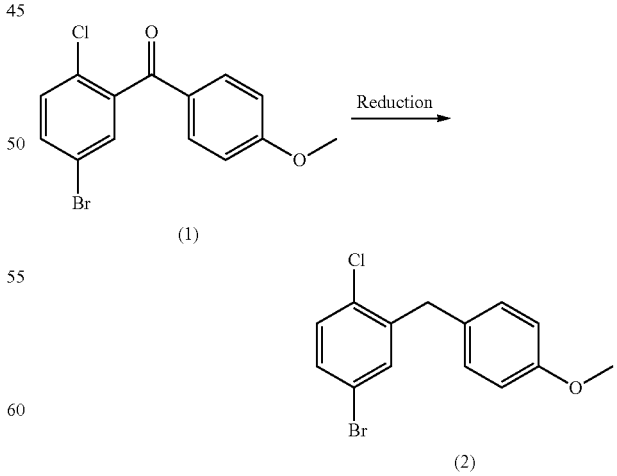

(b) coupling the diphenylmethane compound (2) with a protected gluconolactone (3), followed by treatment with an acid to obtain a compound (4);

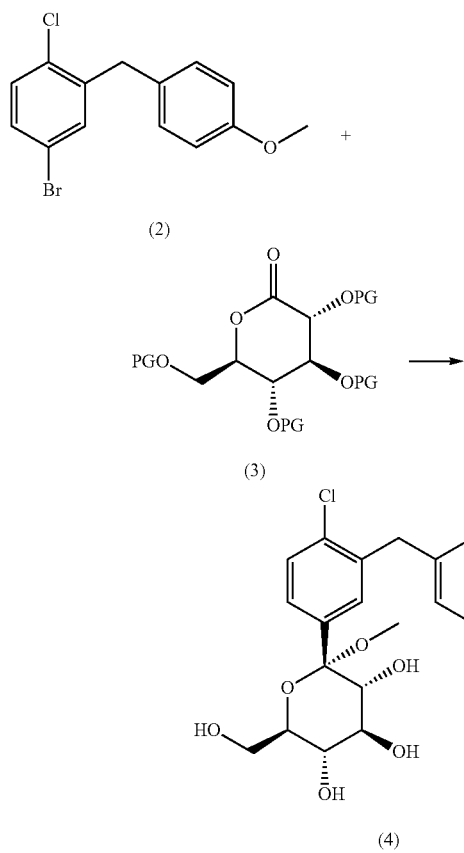

(2)

(3)

wherein in compound (3), PG is a hydroxyl protecting group;

(c) treating the compound (4) with a suitable reagent, wherein the hydroxy groups are protected to form a compound (5), wherein PG denotes a hydroxyl protecting group;

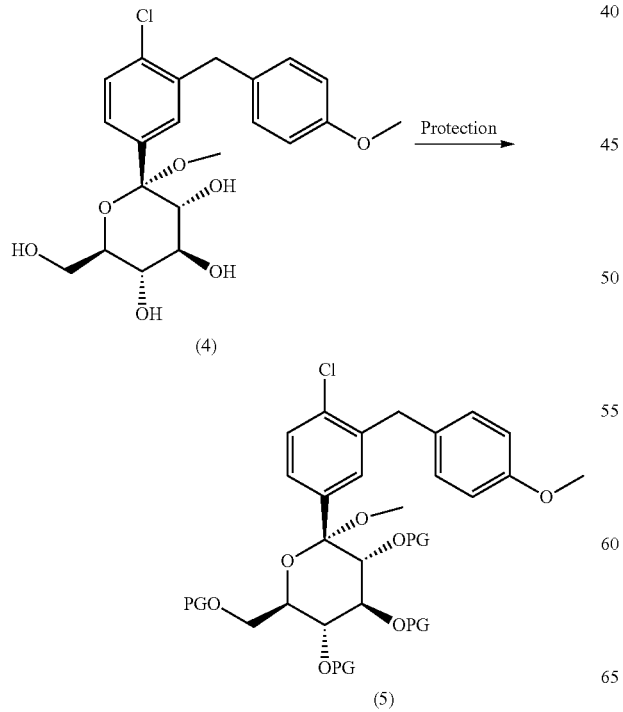

(4)

(5)

or reducing the compound (4) obtained from step (b) to obtain a compound 5a;

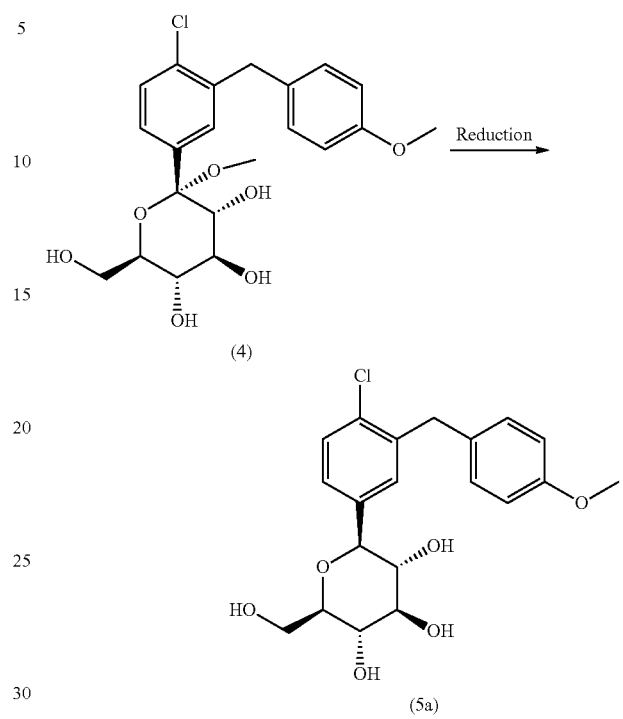

(4)

(5a)

(d) reacting the compound (5) obtained from step (c) with a reducing agent to form a compound (6);

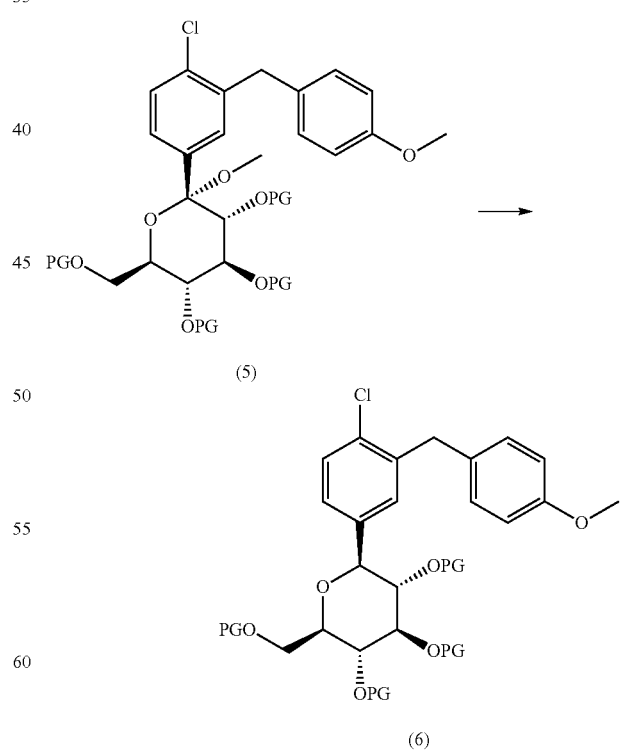

(5)

(6)

or reacting the compound (5a) obtained from step (c) with suitable reagent to protect the hydroxy groups to form a compound (6);

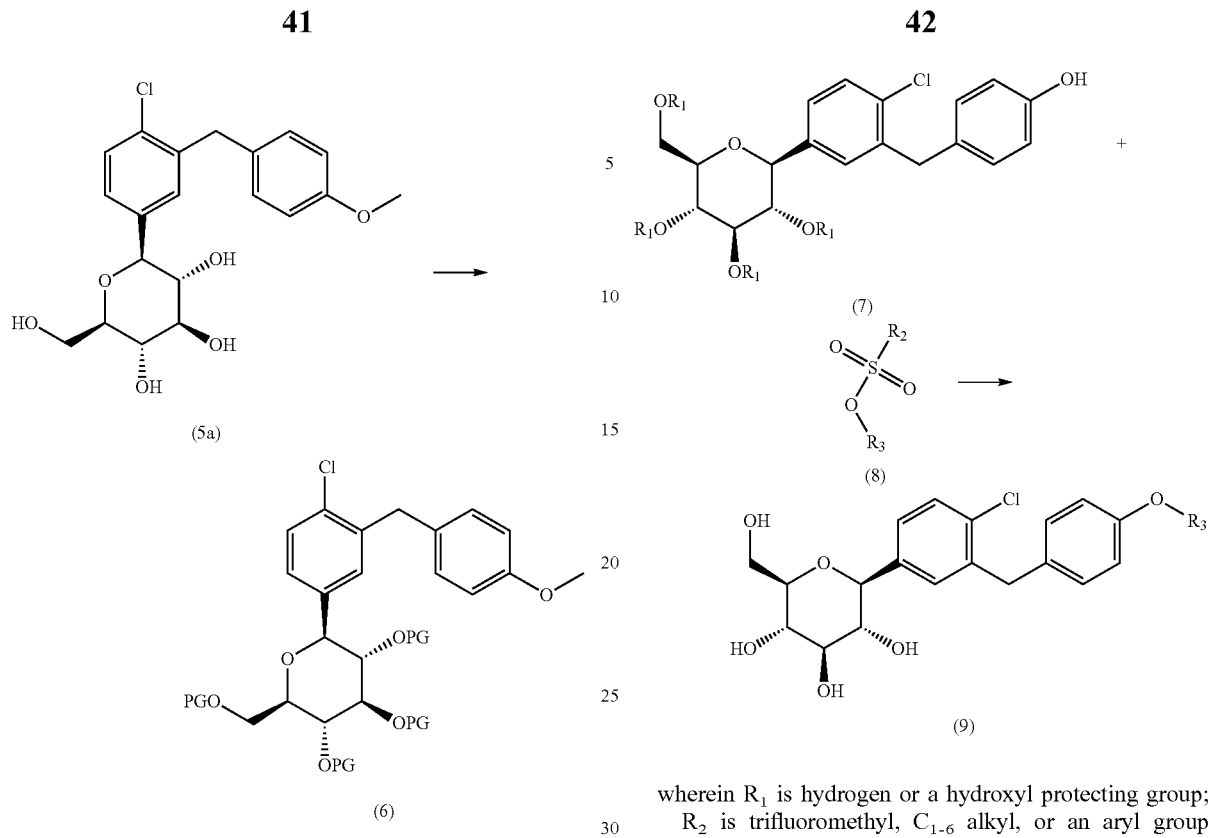

(e) subjecting the compound (6) to O-demethylation in the presence of a reagent-pair, wherein R₁ is hydrogen or a hydroxyl protecting group (PG); and

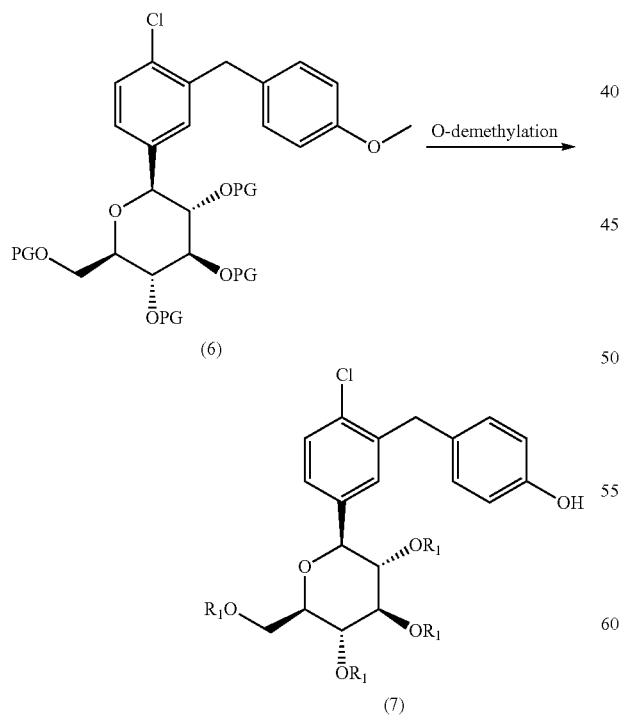

(f) reacting the compound (7) with a compound (8) to obtain the compound (9);

wherein $R_1$ is hydrogen or a hydroxyl protecting group; $R_2$ is trifluoromethyl, $C_{1-6}$ alkyl, or an aryl group optionally substituted at para position with halogen or $C_{1-6}$ alkyl; and $R_3$ is tetrahydrofuran-3-yl or ethyl.

2. The process according to claim 1, wherein the reduction in step (a), step (c) and step (d) is carried out using silanes selected from the group consisting of triethylsilane, tripropylsilane, triisopropylsilane, or diphenylsilane, sodium borohydride, sodium cyanoborohydride, zinc borohydride, borane complexes, lithium aluminum hydride, diisobutylaluminum hydride, and vitride; Lewis acid selected from the group consisting of aluminum chloride, boron trifluorideetherate ($BF_3 \cdot Et_2O$), copper (II) triflate, iron (III) chloride, tin (II) chloride, tin tetrachloride and zinc chloride; or Bronsted acids selected from the group consisting of hydrochloric acid, toluenesulfonic acid, trifluoroacetic acid and acetic acid;

the coupling in step (b) is carried out using alkyllithium selected from the group consisting of n-, sec-, and tert-butyl lithium; the acid is selected from methanesulfonic acid, toluenesulfonic acid, hydrochloric acid, sulphuric acid, acetic acid, and ammonium chloride;

the suitable reagent in step (c) and step (d) for introducing the hydroxyl protecting group is selected from acetic anhydride, acetyl chloride, propionic anhydride, propanoyl chloride, benzoic anhydride, benzoyl chloride and 4-nitrobenzoyl chloride;

the reagent pair in step (e) is thiourea/$AlCl_3$ reagent pair; and the O-demethylation is carried out using reagents selected from the group consisting of dodecanethiol, decanethiol, cyclohexane thiol, cyclopentanethiol, cyclobutanethiol, thiophenol, methanethiol, ethanethiol, 1-propanethiol, 2-propanethiol, n-butanethiol, tert-butanthiol, furan-2-yl-methanethiol, ethandithiol, 1,2-propanedithiol, 1,3-propanedithiol, 1,3-butanedithiol, and 1,4-butanedithiol.

3. The process according to claim 1, wherein the process for preparing the compound (7) comprises:

(a) reacting compound (1) with sodium borohydride in the presence of aluminium chloride and tetrahydrofuran to obtain diphenylmethane compound (2);

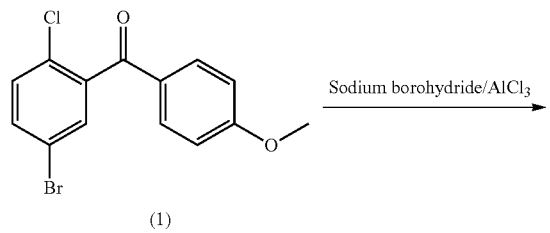

(1)

(2)

(b) coupling the diphenylmethane compound (2) with protected gluconolactone (3) in the presence of n-butyllithium and tetrahydrofuran, followed by treatment with methanesulfonic acid in methanol to obtain compound (4);

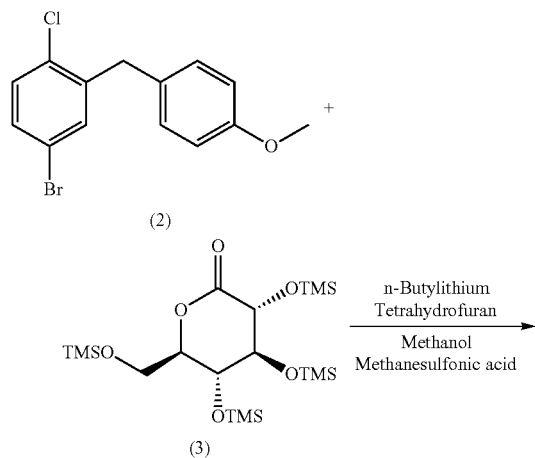

(2)

(3)

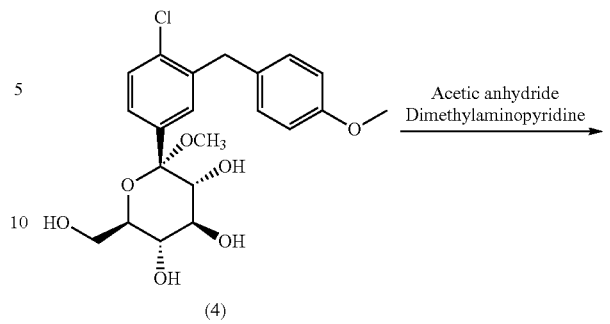

(4)

(5)

or reducing the compound (4) obtained from step (b) using triethylsilane and boron trifluorideetherate to obtain compound 5a;

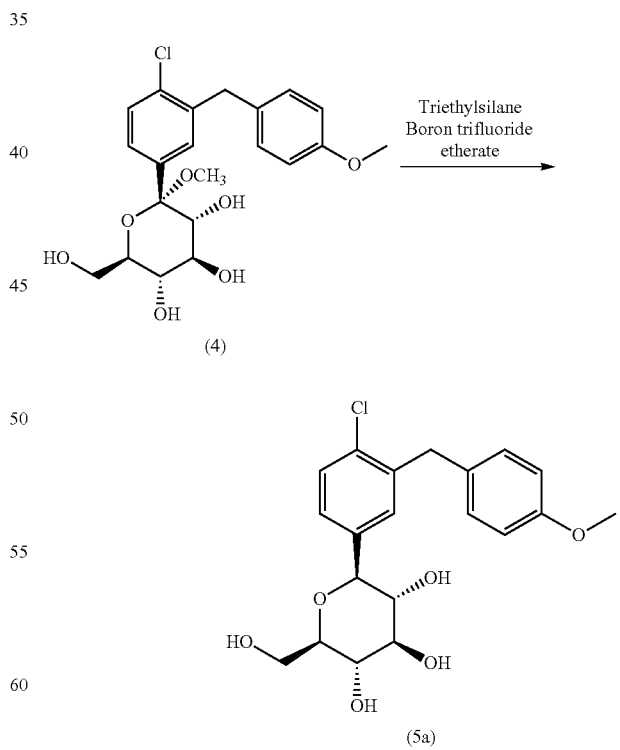

(4)

(5a)

(c) treating compound (4) with acetic anhydride in the presence of N,N-dimethylaminopyridine, wherein the hydroxy groups are protected to form compound (5);

(d) reacting the compound (5) obtained from step (c) with triethylsilane in the presence of borontrifluorideetherate and dichloromethane to form compound (6);

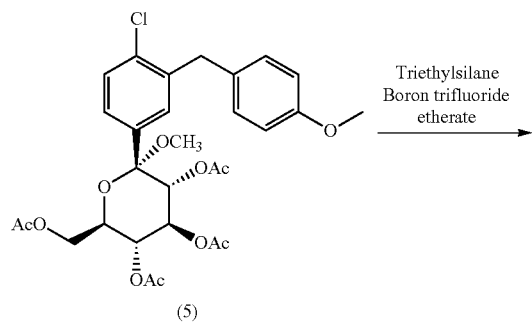

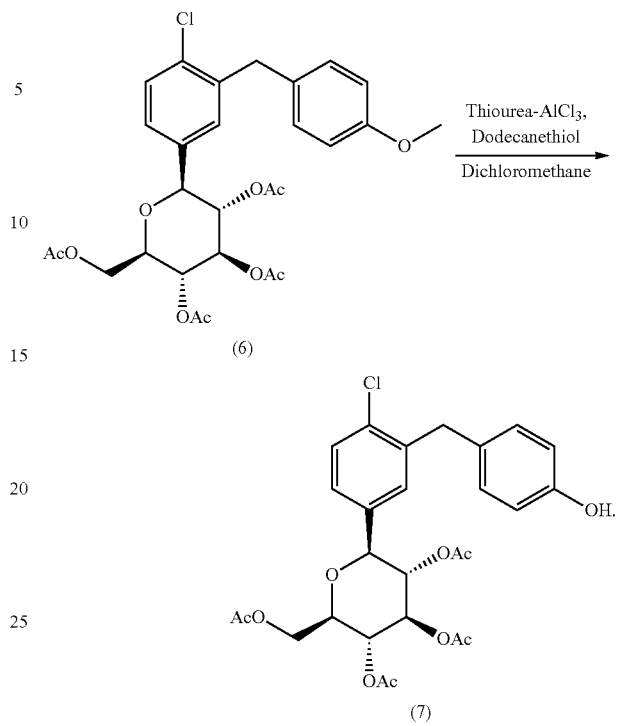

or reacting the compound (5a) obtained from step (c) with acetic anhydride to protect the hydroxy groups in the presence of N,N-dimethylaminopyridine to form compound (6);

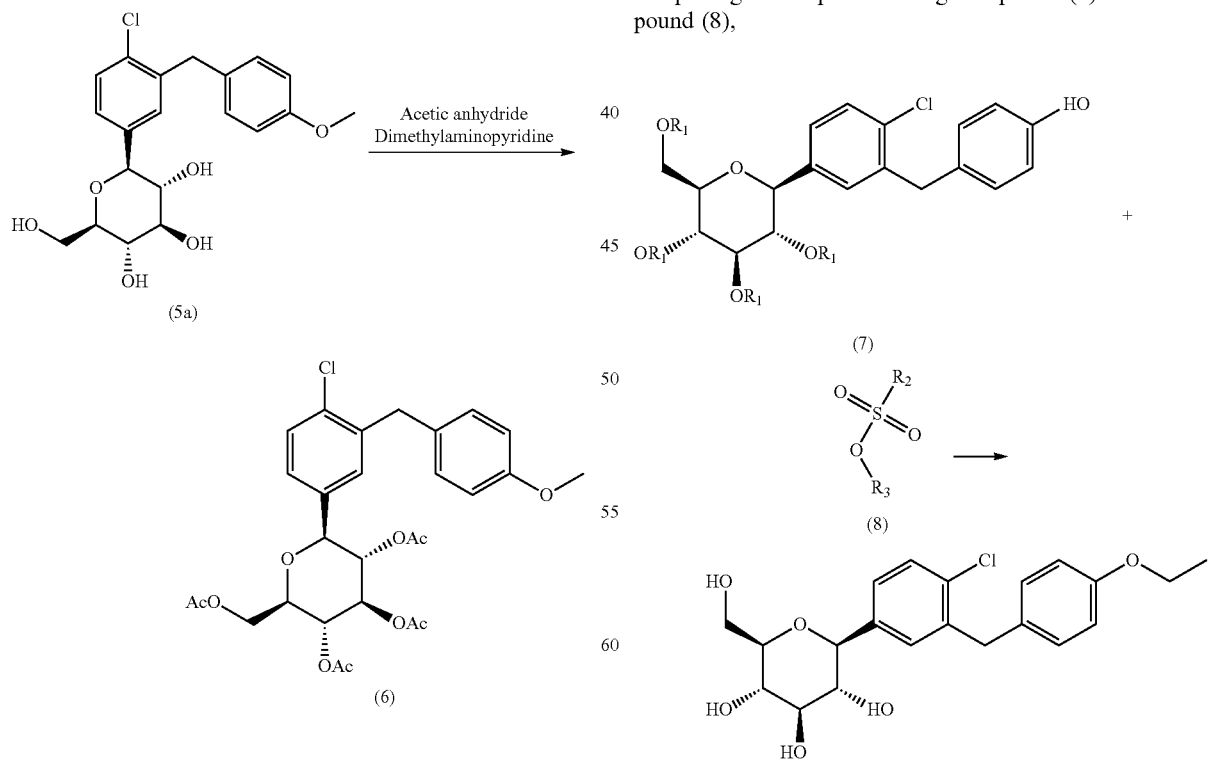

(e) subjecting the compound (6) to O-demethylation in the presence of thiourea-AlCl$_3$ reagent pair and dodecanethiol to form compound (7), 4. The process according to claim 1, wherein the compound (9) is (1S)-1,5-anhydro-1-C-[4-chloro-3-[(4-ethoxyphenyl)methyl] phenyl]-D-glucitol, dapagliflozin (compound 9b) and the process for preparing the compound 9b comprising the step of reacting compound (7) with compound (8), wherein $R_1$ is hydrogen or hydroxyl protecting group; $R_2$ is trifluoromethyl, $C_{1-6}$ alkyl, or an aryl group optionally substituted at para position with halogen, or $C_{1-6}$ alkyl and $R_3$ is ethyl.

5. The process according to claim 1, wherein the compound (9) is (1S)-1,5-anhydro-1-C-[4-chloro-3-[[4-[[(3S)-tetrahydro-3-furanyl]oxy]phenyl]methyl]phenyl]-D-glucitol, empagliflozin (9a) and the process for preparing the compound 9a comprising the step of reacting compound (7) with compound (8),

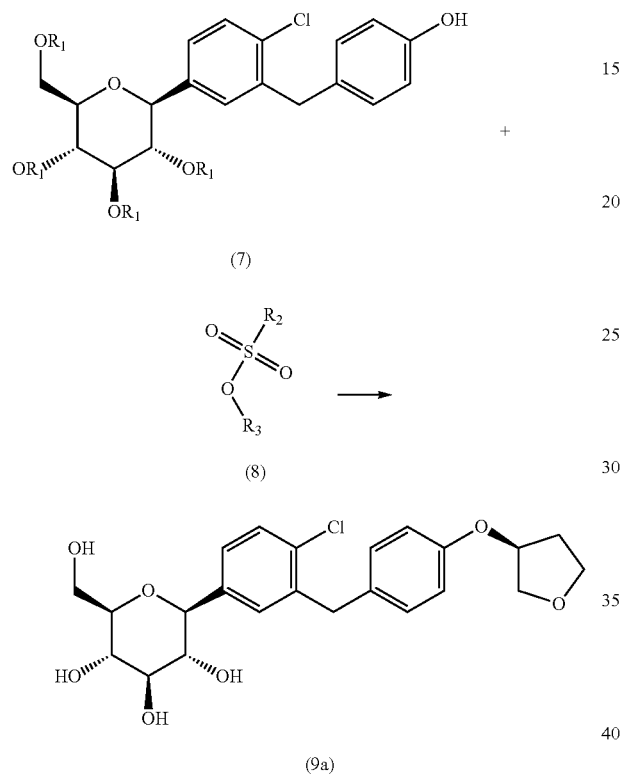

wherein $R_1$ is hydrogen or hydroxyl protecting group; $R_2$ is trifluoromethyl, $C_{1-6}$ alkyl, or an aryl group optionally substituted at para position with halogen or $C_{1-6}$ alkyl; and $R_3$ is tetrahydrofuran-3-yl.

6. The process according to claim 5, wherein the process further comprising:
(a) dissolving empagliflozin in one or more solvents;
(b) optionally filtering the undissolved particles;
(c) distilling the solvent completely; and
(d) drying to isolate an amorphous empagliflozin.

7. The process for according to claim 5, wherein the process further comprising:
(a) dissolving empagliflozin and a pharmaceutically acceptable polymer in one or more solvents;
(b) optionally filtering the un-dissolved particles;
(c) distilling the solvent completely; and
(d) drying to isolate amorphous solid dispersion of empagliflozin and the polymer; wherein the pharmaceutically acceptable polymer is water soluble polymers selected from the group consisting of polyvinyl pyrrolidone, copovidone, polyvinyl alcohol, hydroxypropyl methylcellulose, hydroxypropyl cellulose, polyethylene glycol, and polyvinyl caprolactam-polyvinyl acetate-polyethylene glycol copolymers, or water insoluble polymers selected from the group consisting of methylcellulose, ethylcellulose, polymethacrylates, hypromellose phthalate, hypromellose succinate, hypromellose acetate succinate (HPMC AS), cellulose acetate phthalate, and carboxymethyl ethyl cellulose; the solvent is selected from the group consisting of hydrocarbon solvents, ether solvents, ester solvents, polar aprotic solvents, chlorinated solvents, nitrile solvents, alcoholic solvents, polar solvents and mixtures thereof.

8. A process for preparing a compound (8), in desired R configuration, comprising:
(a) reacting (S)-3-hydroxytetrahydrofuran with compound ii to form a compound iii;

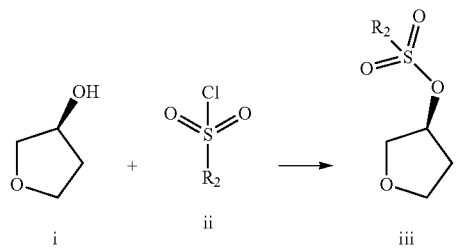

wherein $R_2$ is $C_{1-6}$ alkyl, trifluoromethyl or an aryl group optionally substituted at para position with halogen, nitro, or $C_{1-6}$ alkyl;

(b) treating the compound iii with an alkali metal acetate selected from the group consisting of lithium acetate, sodium acetate, potassium acetate and cesium acetate, optionally in the presence of a phase transfer catalyst to form a compound iv;

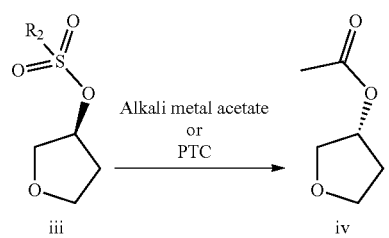

wherein $R_2$ is defined as hereinbefore;

(c) subjecting the compound iv to hydrolysis to form a compound v, (R)-3-hydroxy tetrahydrofuran;

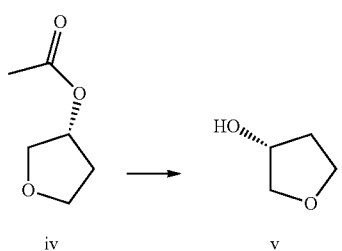

(d) treating the compound v, (R)-3-hydroxytetrahydrofuran with compound ii to form the compound (8);

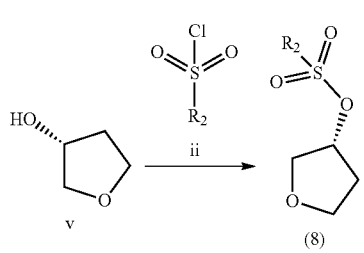

wherein $R_2$ is $C_{1-6}$alkyl, trifluoromethyl or an aryl group optionally substituted at para position with halogen or $C_{1-6}$ alkyl.

9. The process according to claim 8, wherein the process comprises:
   (a) reacting (S)-3-hydroxytetrahydrofuran with compound ii to form a compound iii;

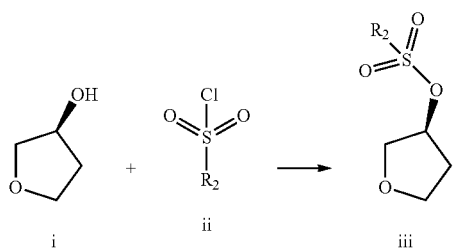

wherein $R_2$ is $C_{1-6}$ alkyl, trifluoromethyl or an aryl group optionally substituted at para position with halogen, nitro, or $C_{1-6}$ alkyl;

(b) treating the compound iii with an alkali metal acetate in the presence of a phase transfer catalyst to form a compound iv;

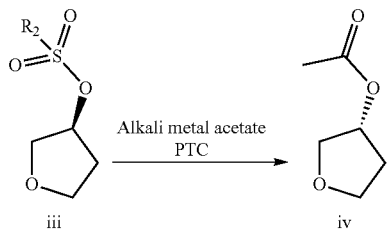

wherein $R_2$ is defined as hereinbefore; the alkali metal acetate is selected from the group consisting of lithium acetate, sodium acetate, potassium acetate, and cesium acetate; the phase transfer catalyst is crown ethers selected from the group consisting of 12-crown-4, 15-crown-5, and 18-crown-6;

(c) subjecting the compound iv to hydrolysis to form a compound v, (R)-3-hydroxy tetrahydrofuran;

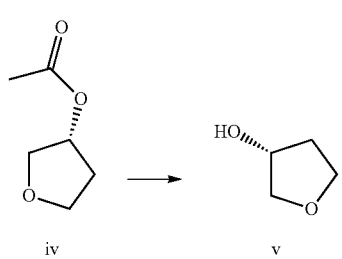

(d) treating the compound v, (R)-3-hydroxytetrahydrofuran with compound ii to form the compound (8);

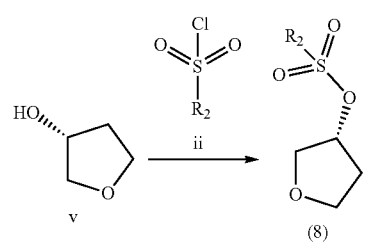

wherein $R_2$ is $C_{1-6}$ alkyl, trifluoromethyl or an aryl group optionally substituted at para position with halogen, or $C_{1-6}$ alkyl.

10. A process for preparing (1S)-1,5-anhydro-1-C-[4-chloro-3-[[4-[[(3S)-tetrahydro-3-furanyl]oxy]phenyl]methyl]phenyl]-D-glucitol, empagliflozin, wherein the process comprises:
   (a) reacting a compound of formula V with a compound B to obtain a compound of formula VI;

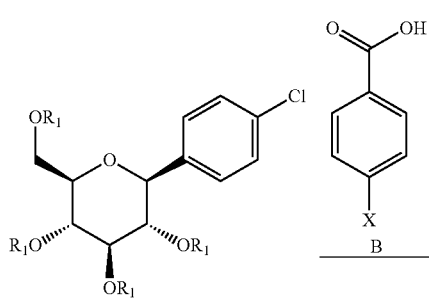

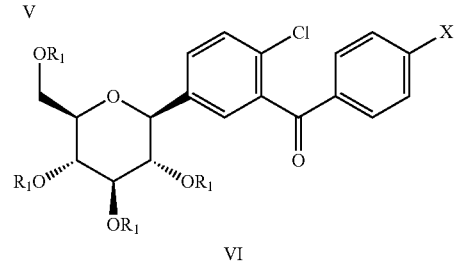

wherein $R_1$ is a hydroxyl protecting group selected from acetyl, propionyl, pivaloyl, and benzoyl; X is a leaving group selected from halogen, mesylate, tosylate, brosylate, besylate, nosylate and triflate;

(b) coupling the compound of formula VI with tetrahydrofuran-3-ol (C) to obtain a compound of formula VIIa;

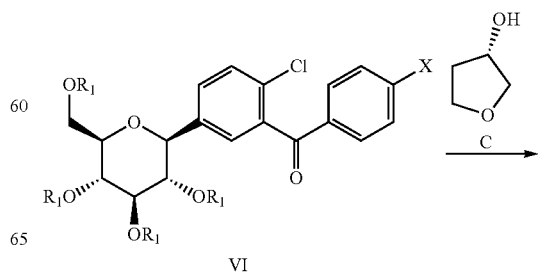

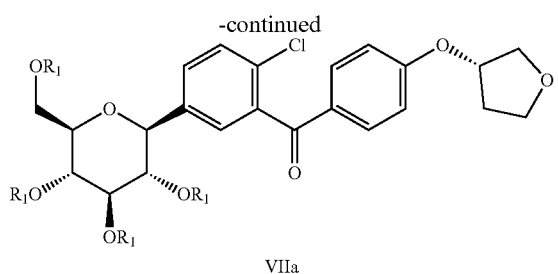

VIIa (c) hydrolyzing the compound of formula VIIa to obtain a compound of formula VII; and

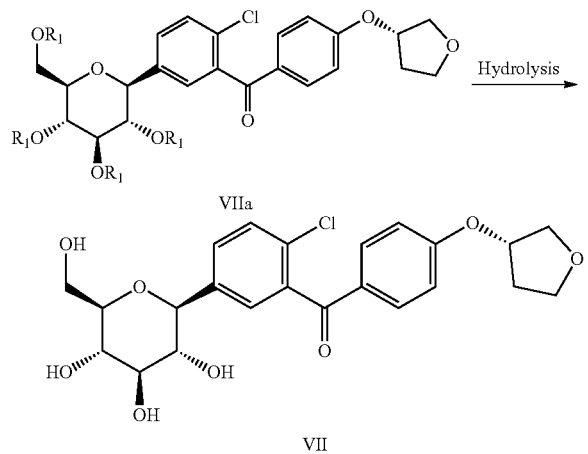

(d) reducing the compound of formula VII to yield empagliflozin;

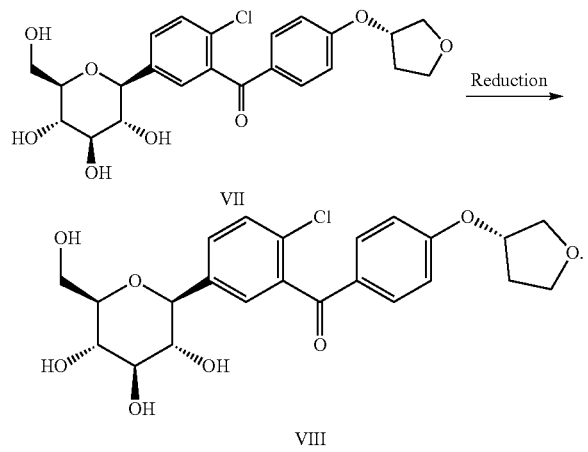

11. The process according to claim 10, wherein in step (a), the compound B is converted to corresponding acyl halide and reacted with compound V in the presence of a leis acid selected from the group consisting of aluminum chloride, iron (III) chloride, zinc chloride and boron trifluorideetherate;

in step (b), the coupling is carried out in the presence of base selected from the group consisting of sodium hydride, sodium hydroxide, sodium methoxide, sodium ethoxide, lithium hydroxide, potassium hydroxide, and potassium tertiary-butoxide;

in step (d), the reduction is carried out with a reducing agent; wherein the reducing agent is silanes selected from the group consisting of triethylsilane, tripropylsilane, triisopropylsilane, or diphenylsilane; sodium borohydride, sodium cyanoborohydride, zinc borohydride, borane complexes, lithium aluminum hydride, and diisobutylaluminum hydride; optionally in the presence of lewis acid selected from the group consisting of boron trifluorideetherate, tin (II) chloride, trimethylsilyltriflate, titanium tetrachloride, tin tetrachloride, copper (II) triflate, and zinc iodide.

12. Compounds of formula VI, VIIa and VII obtained according to the process of claim 10, wherein $R_1$ is a hydroxyl protecting group and X is a leaving group selected from halogen, mesylate, tosylate, brosylate, besylate, nosylate and triflate;

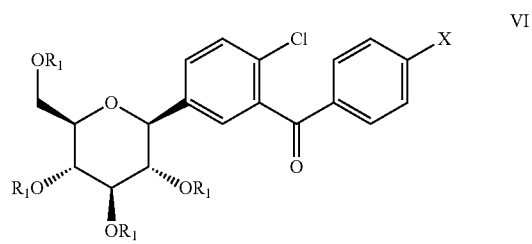

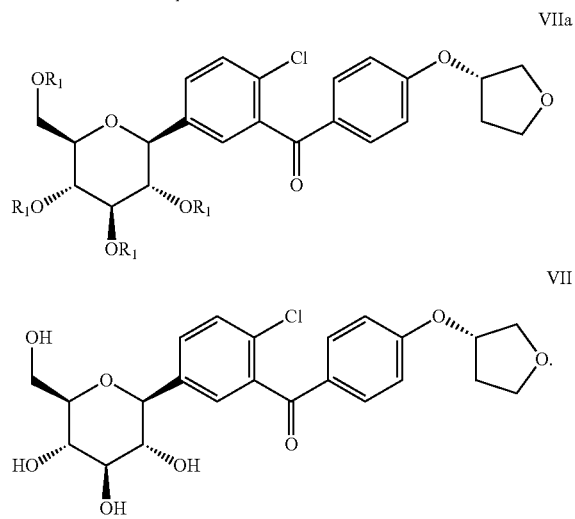

* * * * *